(12) United States Patent
Ma et al.

(10) Patent No.: US 11,648,558 B2
(45) Date of Patent: May 16, 2023

(54) BIOSENSOR APPARATUS, METHOD OF FABRICATING BIOSENSOR APPARATUS, BIOSENSOR CHIP, AND METHOD OF DETECTING TARGET MOLECULE

(71) Applicant: BOE Technology Group Co., Ltd., Beijing (CN)

(72) Inventors: Xiaochen Ma, Beijing (CN); Guangcai Yuan, Beijing (CN); Ce Ning, Beijing (CN); Xin Gu, Beijing (CN); Hehe Hu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 725 days.

(21) Appl. No.: 16/605,776

(22) PCT Filed: May 6, 2019

(86) PCT No.: PCT/CN2019/085699
§ 371 (c)(1),
(2) Date: Oct. 16, 2019

(87) PCT Pub. No.: WO2020/082721
PCT Pub. Date: Apr. 30, 2020

(65) Prior Publication Data
US 2021/0331168 A1    Oct. 28, 2021

(30) Foreign Application Priority Data
Oct. 23, 2018    (CN) .......................... 201811237709.8

(51) Int. Cl.
*B01L 3/00* (2006.01)
*G01N 27/12* (2006.01)
*G01N 33/487* (2006.01)

(52) U.S. Cl.
CPC ... *B01L 3/502761* (2013.01); *B01L 3/502707* (2013.01); *G01N 27/128* (2013.01);
(Continued)

(58) Field of Classification Search
CPC ......... B01L 3/502761; B01L 3/502707; B01L 2200/0647; B01L 2200/12;
(Continued)

(56) References Cited

U.S. PATENT DOCUMENTS

| 7,250,115 | B2 * | 7/2007 | Barth | ............... G01N 33/48721 216/41 |
| 2009/0142825 | A1 * | 6/2009 | Murray | ............ G01N 33/54373 430/311 |
| 2014/0367749 | A1 * | 12/2014 | Bai | ................. H01L 21/823871 257/253 |

* cited by examiner

*Primary Examiner* — Narayan K Bhat
(74) *Attorney, Agent, or Firm* — Intellectual Valley Law, P.C.

(57) ABSTRACT

A biosensor apparatus is provided. The biosensor apparatus includes a base substrate; a first fluid channel layer on the base substrate and having a first fluid channel passing therethrough; a foundation layer on a side of the first fluid channel layer away from the base substrate, a foundation layer throughhole extending through the foundation layer to connect to the first fluid channel; and a micropore layer on a side of the foundation layer away from the base substrate, a micropore extending through the micropore layer to connect to the first fluid channel through the foundation layer throughhole. The micropore layer extends into the foundation layer throughhole and at least partially covers an inner wall of the foundation layer throughhole.

18 Claims, 18 Drawing Sheets

(52) U.S. Cl.
CPC ... *B01L 2200/0647* (2013.01); *B01L 2200/12* (2013.01); *B01L 2300/0645* (2013.01); *B01L 2300/0864* (2013.01); *B01L 2300/0887* (2013.01); *B01L 2300/12* (2013.01); *B01L 2400/0421* (2013.01); *G01N 33/48721* (2013.01)

(58) Field of Classification Search
CPC ..... B01L 2300/0645; B01L 2300/0864; B01L 2300/0887; B01L 2300/12; B01L 2400/0421; B01L 2300/0896; G01N 27/128; G01N 33/48721; G01N 35/00
See application file for complete search history.

BIOSENSOR APPARATUS, METHOD OF FABRICATING BIOSENSOR APPARATUS, BIOSENSOR CHIP, AND METHOD OF DETECTING TARGET MOLECULE

CROSS-REFERENCE TO RELATED APPLICATION

This application is a national stage application under 35 U.S.C. § 371 of International Application No. PCT/CN2019/085699, filed May 6, 2019, which claims priority to Chinese Patent Application No. 201811237709.8, filed Oct. 23, 2018. Each of the forgoing applications is herein incorporated by reference in its entirety for all purposes.

TECHNICAL FIELD

The present invention relates to biosensor technology, more particularly, to a biosensor apparatus, a method of fabricating a biosensor apparatus, a biosensor chip, and a method of detecting a target molecule.

BACKGROUND

Microfluidics deals with the behavior, precise control and manipulation of fluids that are geometrically constrained to a small, typically sub-millimeter or sub-micron, scale at which capillary penetration governs mass transport. It is a multidisciplinary field at the intersection of engineering, physics, chemistry, biochemistry, nanotechnology, and biotechnology, with practical applications in the design of systems in which low volumes of fluids are processed to achieve multiplexing, automation, and high-throughput screening. Microfluidics emerged in the beginning of the 1980s and is used in the development of inkjet printheads, DNA chips, lab-on-a-chip technology, micro-propulsion, and micro-thermal technologies.

SUMMARY

In one aspect, the present invention provides a biosensor apparatus comprising a base substrate; a first fluid channel layer on the base substrate and having a first fluid channel passing therethrough; a foundation layer on a side of the first fluid channel layer away from the base substrate, a foundation layer throughhole extending through the foundation layer to connect to the first fluid channel; and a micropore layer on a side of the foundation layer away from the base substrate, a micropore extending through the micropore layer to connect to the first fluid channel through the foundation layer throughhole; wherein the micropore layer extends into the foundation layer throughhole and at least partially covers an inner wall of the foundation layer throughhole.

Optionally, the foundation layer comprises a conductive material; and the micropore layer comprises an insulating material; wherein the biosensor apparatus further comprises a first conductive layer on a side of the micropore layer away from file base substrate.

Optionally, the first conductive layer is a unitary electrode, a first conductive layer throughhole extending through the first conductive layer to connect to the micropore.

Optionally, the first conductive layer comprises two block electrodes spaced apart from each other and on two opposite side of a periphery of the micropore.

Optionally, the foundation layer comprises an insulating material; the micropore layer comprises an insulating material. The biosensor apparatus further comprises: a detection electrode in the first fluid channel; and a second conductive layer on a side of the micropore layer away from the base substrate.

Optionally, the foundation layer comprises an insulating material. The micropore layer comprises an insulating material. The biosensor apparatus further comprises a semiconductor layer on a side of the micropore layer away from the base substrate, a semiconductor layer throughhole extending through the semiconductor layer to connect to the micropore.

Optionally, the foundation layer comprises an insulating material. The micropore layer comprises a semiconductor material. The biosensor apparatus further comprises a third conductive layer on a side of the micropore layer away from the base substrate. The third conductive layer comprises two block electrodes spaced apart from each other and on two opposite side of a periphery of the micropore.

Optionally, the foundation layer comprises an insulating sub-layer on a side of the first fluid channel layer away from the base substrate, the insulating sub-layer comprising an insulating material; and a conductive sub-layer on a side of the insulating sub-layer away from the base substrate, the conductive sub-layer comprising a conductive material; wherein the foundation layer is divided into two parts spaced apart from each other by the foundation layer throughhole and a split gap connected to the foundation layer throughhole; and the micropore layer extends into the split gap and fills in the split gap.

Optionally, the biosensor apparatus further comprises a capping layer covering an outmost conductive layer of the biosensor apparatus.

Optionally, the biosensor apparatus further comprises a second fluid channel layer on a side of the micropore layer away from the base substrate and having a second fluid channel passing therethrough, the second fluid channel connected to the micropore.

In another aspect, the present invention provides a method of fabricating a biosensor apparatus comprising forming a first fluid channel layer on the base substrate and having a first fluid channel passing therethrough; forming a foundation layer on a side of the first fluid channel layer away from the base substrate, a foundation layer throughhole formed to extend through the foundation layer to connect to the first fluid channel; and forming a micropore layer on a side of the foundation layer away from the base substrate, a micropore formed to extend through the micropore layer to connect to the first fluid channel through the foundation layer throughhole; wherein the micropore layer is formed to extend into the foundation layer throughhole and at least partially covers an inner wall of the foundation layer throughhole.

Optionally, forming the first fluid channel layer and forming the foundation layer comprise forming a first fluid channel material layer on a base substrate; forming a foundation material layer on a side of the first fluid channel material layer away from the base substrate; patterning the foundation material layer to form the foundation layer, the foundation layer formed to have the foundation layer throughhole extending therethrough; and patterning the first fluid channel material layer to form the first fluid channel layer, the first fluid channel layer formed to have the first fluid channel passing therethrough, the foundation layer throughhole formed to connect to the first fluid channel; wherein forming the micropore layer comprises depositing a micropore layer material on a side of the foundation layer away from the base substrate; wherein the micropore layer material is deposited onto an inner wall of the foundation layer throughhole.

Optionally, the foundation layer is formed using a conductive material; and the micropore layer is formed using an insulating material; wherein the method further comprises, subsequent to forming the micropore layer, forming a first conductive layer on a side of the micropore layer away from the base substrate.

Optionally, the foundation layer is formed using an insulating material; and the micropore layer is formed using an insulating material; wherein the method further comprises, prior to forming the first fluid channel layer, forming a detection electrode on the base substrate; and subsequent to forming the micropore layer, forming a second conductive layer on a side of the micropore layer away from the base substrate.

Optionally, the foundation layer is formed using an insulating material; and the micropore layer is formed using an insulating material; wherein the method further comprises, subsequent to forming the micropore layer, forming a semiconductor layer on a side of the micropore layer away from the base substrate, a semiconductor layer throughhole formed to extend through the semiconductor layer to connect to the micropore.

Optionally, the foundation layer is formed using an insulating material; and the micropore layer is formed using a semiconductor material; wherein the method further comprises, subsequent to forming the micropore layer, forming a third conductive layer on a side of the micropore layer away from the base substrate, the third conductive layer formed to comprise two block electrodes spaced apart from each other and on two opposite side of a periphery of the micropore.

Optionally, the micropore layer is formed using an insulating material; wherein forming the foundation layer comprises forming an insulating sub-layer on a side of the first fluid channel layer away from the base substrate, the insulating sub-layer formed using an insulating material; and forming a conductive sub-layer on a side of the insulating sub-layer away from the base substrate, the conductive sub-layer formed using a conductive material; wherein the foundation layer is formed as two parts spaced apart from each other by the foundation layer throughhole and a split gap connected to the foundation layer throughhole; and the micropore layer is formed to extend into the split gap and fill in the split gap.

Optionally, the method further comprises forming a capping layer covering an outmost conductive layer of the biosensor apparatus.

Optionally, subsequent to forming the micropore layer, the method further comprises forming a second fluid channel layer on a side of the micropore layer away from the base substrate and having a second fluid channel passing therethrough, the second fluid channel formed to connect to the micropore.

In another aspect, the present invention provides a biosensor chip comprising the biosensor apparatus described herein.

In another aspect, the present invention provides a method of detecting a target molecule comprising providing the biosensor apparatus described herein; driving a microfluid comprising the target molecule to pass through the micropore; detecting an electrical signal change at the micropore as the target molecule passing through the micropore using an electrical signal detector; and analyzing the electrical signal change, thereby detecting the target molecule.

BRIEF DESCRIPTION OF THE FIGURES

The following drawings are merely examples for illustrative purposes according to various disclosed embodiments and are not intended to limit the scope of the present invention.

DETAILED DESCRIPTION

Figure 1:
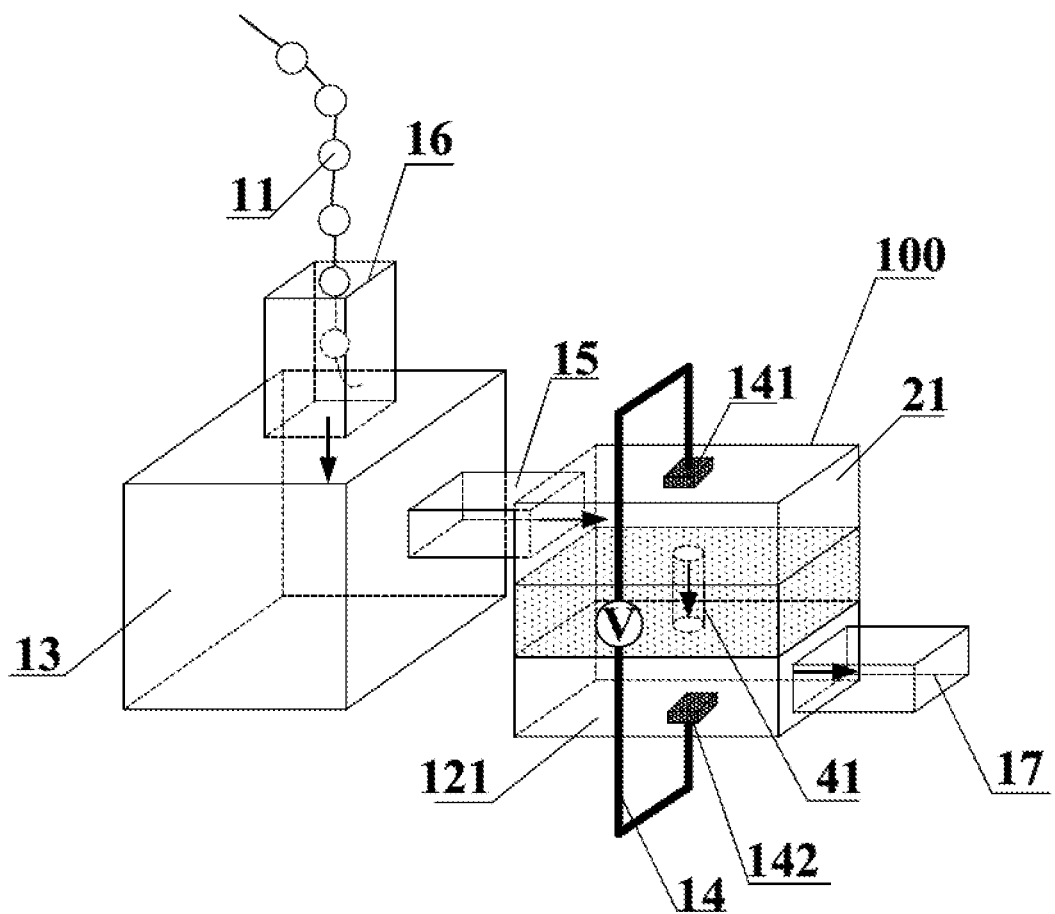
FIG. 1 is a schematic diagram illustrating a structure of a detection system having a biosensor apparatus in some embodiments according to the present disclosure.

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Nanopore sequencing uses electrophoresis to drive a target molecule through an orifice of $10^{-9}$ meters in diameter to sequencing the target molecule. Sequencing is made possible because, when close enough to nanopores, the target molecule causes changes in electrical characteristic of nanopore surfaces.

The nanopore sequencing requires an orifice of $10^{-9}$ meters in diameter to perform the sequencing. In order to fabricate nanopore sequencing apparatus having the orifice of $10^{-9}$ meters in diameter, devices including electron beam exposure devices and precision etching devices should be used to form the orifice of $10^{-9}$ meters in diameter, resulting in a high cost and a low efficiency of fabricating the biosensor for nanopore sequencing. So, it is difficult to achieve mass production of biosensors for nanopore sequencing.

Accordingly, the present disclosure provides, inter alia, a biosensor apparatus, a method of fabricating a biosensor apparatus, a biosensor chip, and a method of detecting a target molecule that substantially obviate one or more of the problems due to limitations and disadvantages of the related art. In one aspect, the present disclosure provides a biosensor apparatus. In some embodiments, the biosensor apparatus includes a base substrate; a first fluid channel layer on the base substrate and having a first fluid channel passing therethrough; a foundation layer on a side of the first fluid channel layer away from the base substrate, a foundation layer throughhole extending through the foundation layer to connect to the first fluid channel; and a micropore layer on a side of the foundation layer away from the base substrate, a micropore extending through the micropore layer to connect to the first fluid channel through the foundation layer throughhole. Optionally, the micropore layer extends into the foundation layer throughhole and at least partially covers an inner wall of the foundation layer throughhole.

As used herein, the term "micropore" refers to pores having cross-sectional dimensions in the range of approximately 1 nm to approximately 1000 µm, e.g., approximately 1 nm to approximately 50 nm, approximately 50 nm to approximately 100 nm, approximately 100 nm to approximately 1 µm, approximately 1 µm to approximately 10 µm, approximately 10 µm to approximately 100 µm, approximately 100 µm to approximately 200 µm, approximately 200 µm to approximately 400 µm, approximately 400 µm to approximately 600 µm, approximately 600 µm to approximately 800 µm, and approximately 800 µm to approximately 1000 µm. The term "cross-sectional dimension" may relate to height, width and in principle also to diameter. When a wall (including a side wall of the pore) of the pore is irregular or curved, the terms "height" and "width" may also relate to mean height and mean width, respectively. A micropore may have any selected cross-sectional shape, for example, U-shaped, D-shaped, rectangular, triangular, elliptical, oval, circular, semi-circular, square, trapezoidal, pentagonal, hexagonal, etc. cross-sectional geometries. Optionally, the micropore has an irregular cross-sectional shape. The geometry may be constant or may vary along the length of the micropore. Further, a micropore may have any selected arrangement or configuration, including linear, non-linear, merging, branching, looped, twisting, stepped, etc. configurations. Optionally, the micropore may have one or more open ends.

In another aspect, the present disclosure also provides a detection system having a biosensor apparatus described herein. FIG. 1 is a schematic diagram illustrating a structure of a detection system having a biosensor apparatus in some embodiments according to the present disclosure. Referring to FIG. 1, in some embodiments, a detection system includes a biosensor apparatus 100, an inlet 16, a driving controller 13, a connecting path 15, a detection circuit 14, and an outlet 17.

Optionally, the detection circuit 14 has a first electrode connection terminal 141, and a second electrode connection terminal 142. Optionally, the biosensor apparatus 100 includes a first fluid channel 21 and a micropore 41.

When the detection system is detecting a target molecule 11, the detection circuit 14 is electrically connected to the biosensor apparatus 100 using the first electrode connection terminal 141 and the second electrode connection terminal 142. For example, a reagent having the target molecule 11 is put into the driving controller 13 through the inlet 16. The driving controller 13 drives the reagent having the target molecule 11 to form a microfluid having the target molecule 11, and drives the microfluid having the target molecule 11 to the biosensor apparatus 100 through the first fluid channel 21. After passing through the biosensor apparatus 100, the microfluid having the target molecule 11 flows out from the outlet 17. During the process of the microfluid passing through the biosensor apparatus 100, the biosensor apparatus 100 and the detection circuit 14 cooperate together to detect the target molecules 11.

Various appropriate ways may be used by the driving controller 13 to drive the microfluid. Examples of ways to drive the microfluid using the driving controller 13 include, but are not limited to, using electrophoresis, and using pressure pump.

Optionally, the detection circuit 14 detects the target molecule 11 by detecting changes of electrical characteristics of the micropore 41, when the target molecule is passing through the micropore 41.

Figure 2A:
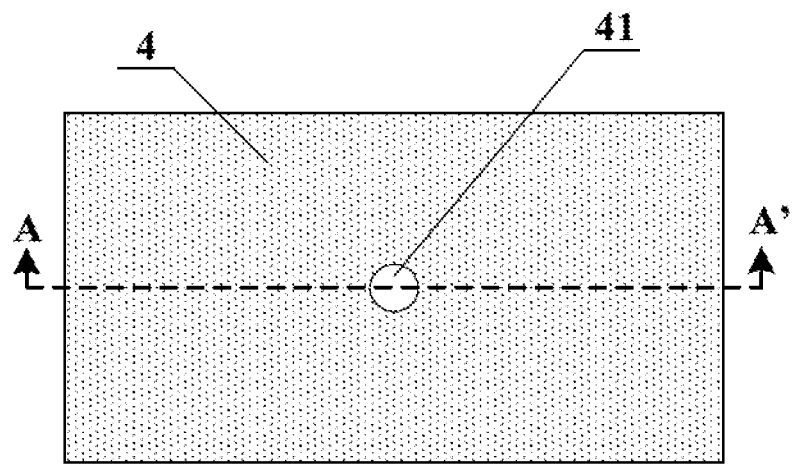
FIG. 2A is a plan view of a biosensor apparatus in some embodiments according to the present disclosure.
Figure 2B:
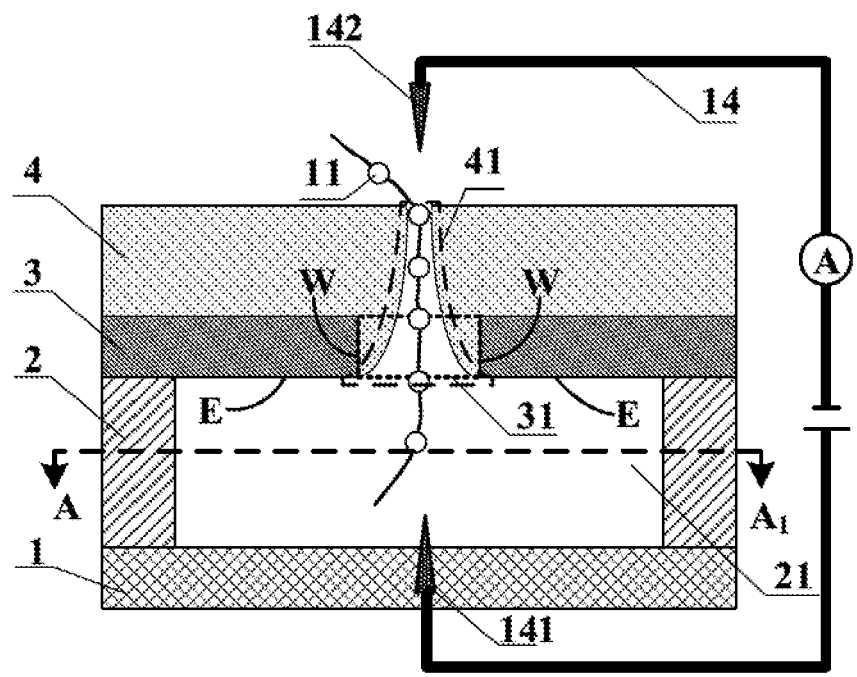
FIG. 2B is a cross-sectional view of a biosensor apparatus along an AA' direction in FIG. 2A.
Figure 2C:
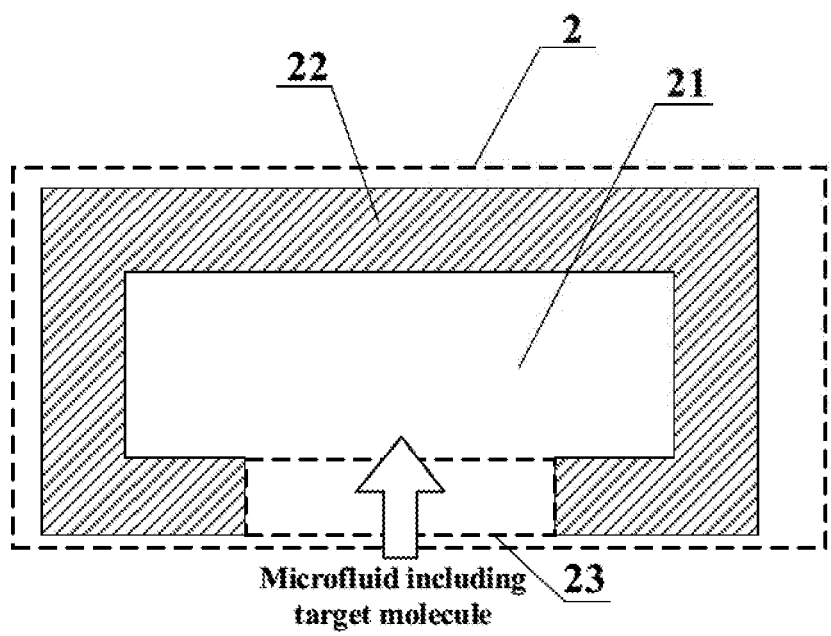
FIG. 2C is a cross-sectional view of a biosensor apparatus along an $AA_1$ direction in FIG. 2B.

In another aspect, the present disclosure provides a biosensor apparatus. FIG. 2A is a plan view of a biosensor apparatus in some embodiments according to the present disclosure. FIG. 2B is a cross-sectional view of a biosensor apparatus along an AA' direction in FIG. 2A. FIG. 2C is a cross-sectional view of a biosensor apparatus along an $AA_1$ direction in FIG. 2B.

Referring to FIG. 2B, the biosensor apparatus includes a base substrate 1; a first fluid channel layer 2 on the base substrate 1 and having a first fluid channel 21 passing therethrough; a foundation layer 3 on a side of the first fluid channel layer 2 away from the base substrate 1, a foundation layer throughhole 31 extending through the foundation layer 3 to connect to the first fluid channel 21; and a micropore layer 4 on a side of the foundation layer 3 away front the base substrate 1, a micropore 41 extending through the micropore layer 4 to connect to the first fluid channel 21 through the foundation layer throughhole 31.

Optionally, the micropore layer 4 extends into the foundation layer throughhole 31 and at least partially covers an inner wall W of the foundation layer throughhole.

In some embodiments, in a region surrounding the micropore 41, an orthographic projection of the micropore layer 4 on the base substrate 1 substantially covers an orthographic projection of the foundation layer 3 on the base substrate 1.

As used herein, the term "substantially covers" refers to one orthographic projection being at least 50%, at least 60%, at least 70%, at least 80%, at least 90%, at least 95%, at least 99%, or 100% covered by another orthographic projection. For example, in the region surrounding the micropore 41, the orthographic projection of the foundation layer 3 on the base substrate 1 is 100% covered by the orthographic projection of the micropore layer 4 on the base substrate 1.

In some embodiments, referring to FIG. 2A and FIG. 2B, a diameter of the micropore 41 gradually increases from a narrowest point of the micropore 41 to an outer edge E of the foundation layer 3 throughhole, along a direction from the micropore layer 4 toward the base substrate 1.

Optionally, the diameter of the micropore 41 is in a range of approximately 1 nm to approximately 1000 μm, e.g. approximately 1 nm to approximately 10 nm, approximately 10 nm to approximately 100 nm, approximately 100 nm to approximately 1000 nm (1 μm), approximately 1000 nm (1 μm) to approximately 10000 nm (10 μm), approximately 10000 nm (10 μm) to approximately 100000 nm (100 μm), and approximately 100000 nm (100 μm) to approximately 1000000 nm (1000 μm).

For example, a diameter of the narrowest point of the micropore 41 is in a range of approximately 1 nm to approximately 1000 μm, e.g. approximately 1 nm to approximately 10 nm, approximately 10 nm to approximately 100 nm, approximately 100 nm to approximately 1000 nm (1 μm), approximately 1000 nm (1 μm) to approximately 10000 nm (10 μm), approximately 10000 nm (10 μm) to approximately 100000 nm (100 μm), and approximately 100000 nm (100 μm) to approximately 1000000 nm (1000 μm).

For example, an average value of diameters of the micropore 41 is in a range of approximately 1 nm to approximately 1000 μm, e.g. approximately 1 nm to approximately 10 nm, approximately 10 nm to approximately 100 nm, approximately 100 nm to approximately 1000 nm (1 μm), approximately 1000 nm (1 μm) to approximately 10000 nm (10 μm), approximately 10000 nm (10 μm) to approximately 100000 nm (100 μm), and approximately 100000 nm (100 μm) to approximately 1000000 nm (1000 μm).

Optionally, the micropore 41 is a nanopore. In one example, the diameter of the micropore 41 is in a range of approximately 1 nm to approximately 50 nm, e.g. approximately 1 nm to approximately 10 nm, approximately 10 nm to approximately 20 nm, approximately 20 nm to approximately 30 nm, approximately 30 nm to approximately 40 nm, and approximately 40 nm to approximately 50 nm. to another example, the diameter of the micropore 41 is in a range of approximately 50 nm to approximately 100 nm, e.g. approximately 50 nm to approximately 60 nm, approximately 60 nm to approximately 70 nm, approximately 70 nm to approximately 80 nm, approximately 80 nm to approximately 90 nm, and approximately 90 nm to approximately 100 nm. In another example, the diameter of the micropore 41 is in a range of approximately 100 nm to approximately 1 μm, e.g. approximately 100 nm to approximately 300 nm, approximately 300 nm to approximately 500 nm, approximately 500 nm to approximately 700 nm, approximately 700 nm to approximately 900 nm, and approximately 900 nm to approximately 1000 nm (1 μm).

In another example, the diameter of the narrowest point of the micropore 41 is in a range of approximately 1 nm to approximately 50 nm, e.g. approximately 1 nm to approximately 10 nm, approximately 10 nm to approximately 20 nm, approximately 20 nm to approximately 30 nm, approximately 30 nm to approximately 40 nm, and approximately 40 nm to approximately 50 nm. In another example, the diameter of the narrowest point of the micropore 41 is in a range of approximately 50 nm to approximately 100 nm, e.g. approximately 50 nm to approximately 60 nm, approximately 60 nm to approximately 70 nm, approximately 70 nm to approximately 80 nm, approximately 80 nm to approximately 90 nm, and approximately 90 nm to approximately 100 nm. In another example, the diameter of the narrowest point of the micropore 41 is in a range of approximately 100 nm to approximately 1 μm, e.g. approximately 100 nm to approximately 300 nm, approximately 300 nm to approximately 500 nm, approximately 500 nm to approximately 700 nm, approximately 700 nm to approximately 900 nm, and approximately 900 nm to approximately 1000 nm (1 μm).

In another example, the average value of diameters of the micropore 41 is in a range of approximately 1 nm to approximately 50 nm, e.g. approximately 1 nm to approximately 10 nm, approximately 10 nm to approximately 20 nm, approximately 20 nm to approximately 30 nm, approximately 30 nm to approximately 40 nm, and approximately 40 nm to approximately 50 nm. In another example, the average value of diameters of the micropore 41 is in a range of approximately 50 nm to approximately 100 nm, e.g. approximately 50 nm to approximately 60 nm, approximately 60 nm to approximately 70 nm, approximately 70 nm to approximately 80 nm, approximately 80 nm to approximately 90 nm, and approximately 90 nm to approximately 100 nm. In another example, the average value of diameters of the micropore 41 is in a range of approximately 100 nm to approximately 1 μm, e.g. approximately 100 nm to approximately 300 nm, approximately 300 nm to approximately 500 nm, approximately 500 nm to approximately 700 nm, approximately 700 nm to approximately 900 nm, and approximately 900 nm to approximately 1000 nm (1 μm).

In some embodiments, referring to FIG. 1, when the biosensor apparatus 100 is configured to detect a target molecule 11, the biosensor apparatus 100 drives a microfluid having the target molecule 11 to enter the first fluid channel 21 and to pass through the micropore 41.

Optionally, referring to FIG. 2B, the detection circuit 14 has a first electrode connection terminal 141, and a second electrode connection terminal 142. In one example, the first electrode connection terminal 141 is electrically connected with an end of the micropore 41 away from the base substrate 1, the second electrode connection terminal 142 is electrically connected with an end of the micropore 41 closer to the base substrate 1. In another example, the first electrode connection terminal 141 is electrically connected with a side of the micropore layer 4 away from the base substrate 1, the second electrode connection terminal 142 is electrically connected with a side of the micropore layer 4 closer to the base substrate 1.

Optionally, the detection circuit 14 further include a power source and an ammeter. Optionally, a current in the detection circuit 14 passes from the first electrode connection terminal 141 to the second electrode connection terminal 142. In one example, no target molecule 11 goes through the micropore 41, the current in the detection circuit 14 remains the same. In another example, the target molecule 11 goes through the micropore 41, the target molecule blocks the passage of current carriers passing though the micropore 41, resulting in a change of the current in the detection circuit 14.

Optionally, different target molecules passing through the micropore 41 cause different changes of the current in the detection circuit 14. By analyzing different changes of the current in the detection circuit 14, the different target molecules passing through the micropore 41 can be detected.

Optionally, the diameter of the micropore 41 is at same scale as a size of the target molecules 11 to allow the target molecules to pass through. In one example, the micropore 41 can filter out molecules having a size bigger than the size of the target molecules 11, which may reduce an influence of non-target molecules on the detection result. In another example, the target molecules can pass through the micropore 41 in order, which may enhance the accuracy of the detection result.

For example, the diameter of the micropore 41 is at a same scale as a diameter of cross-section of a DNA chain having bases, which allows the bases of the DNA passing through the micropore 41 in order, along a DNA chain direction. The diameter of the micropore 41 may prevent a twisted DNA chain from passing through the micropore 41. So, the bases on the DNA chain can be detected in order.

Optionally, the biosensor apparatus can be used in screening processes including drug screening, and cell screening.

Referring to FIG. 2C, in some embodiments, the first fluid channel layer 2 includes the first fluid channel 21 and a first, fluid channel wall 22. Optionally, a microfluidic inlet 23 extends through the first fluid channel wall 22. In one example, the microfluid having the target molecules 11 enters the first fluid channel 21 through the microfluidic inlet 23, and passes out of the first fluid channel 21 through the micropore 41 shown in FIG. 2B. In another example, the microfluid inlet 23 is an outlet. The microfluid having the target molecules passes through the micropore 41, enters the first fluid channel 21, and flows out of the biosensor apparatus.

Figure 3A:
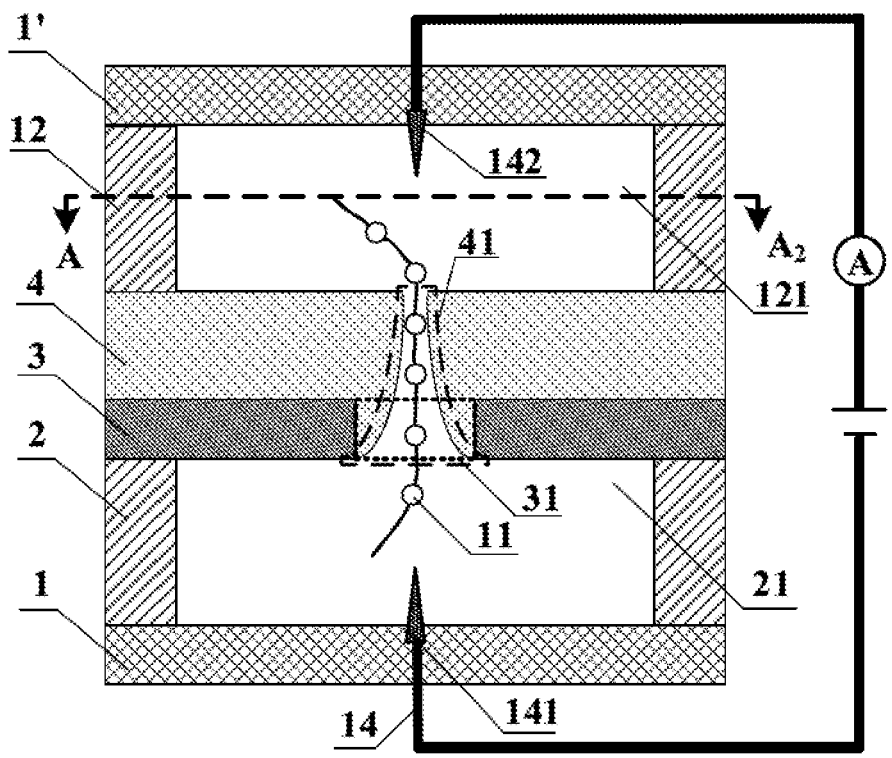
FIG. 3A is a schematic diagram illustrating a structure of a biosensor apparatus in some embodiments according to the present disclosure.
Figure 3B:
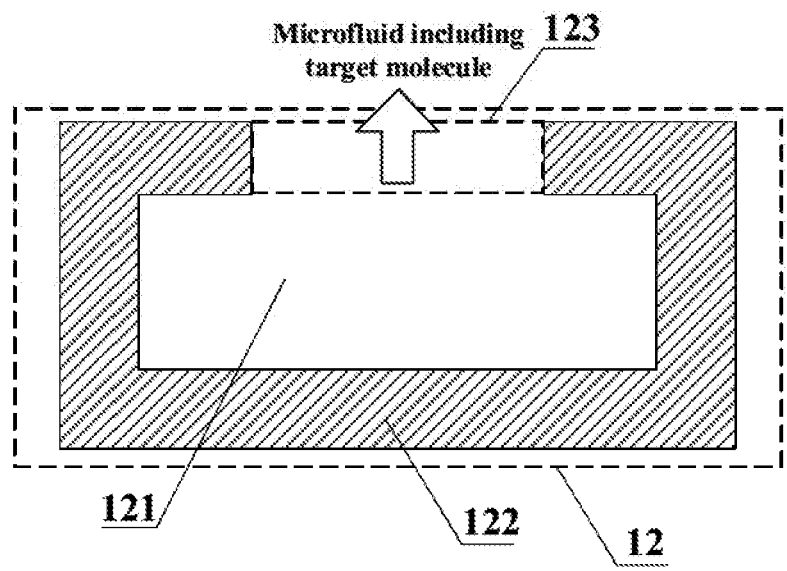
FIG. 3B is a cross-sectional view of a biosensor apparatus along an $AA_2$ direction in FIG. 3A.

FIG. 3A is a schematic diagram illustrating a structure of a biosensor apparatus in some embodiments according to the present disclosure. FIG. 3B is a cross-sectional view of a biosensor apparatus along an $AA_2$ direction in FIG. 3A. Referring to both FIG. 3A and FIG. 3B, in some embodiments, the biosensor apparatus 100 further includes a second fluid channel layer 12 on a side of the micropore layer 4 away from the base substrate 1. Optionally, the second fluid channel layer 12 has a 121 passing through the second fluid channel layer 12. Optionally, the second fluid channel 121 is connected to the micropore 41.

Optionally, referring to FIG. 3B, the second fluid channel layer 12 includes a second fluid channel 121 and a second fluid channel wall 122. Optionally, referring to FIG. 1, FIG. 2C, and FIG. 3B, a microfluid outlet 123 extends through the second fluid channel wall 122.

In one example, the microfluid having the target molecules 11 enters the first fluid channel 21 through the microfluidic inlet 23, passes out of the first fluid channel 21 through the micropore 41, enters the second fluid channel 121, and flows out of the biosensor apparatus through the microfluid outlet 123.

In another example, the microfluid having the target molecules 11 enters the second fluid channel 121 through the microfluidic outlet 123, passes out of the second fluid channel 121 through the micropore 41, enters the first fluid channel 21, and flows out of the biosensor apparatus through the microfluid inlet 23.

Various methods may be used by the biosensor apparatus to detect the target molecule in the microfluid. Optionally, the target molecule in the microfluid can be detected based on changes of current in the detection circuit. Optionally, the target molecule in the microfluid can be detected based on changes of electric potential in the detection circuit. Optionally, the target molecule in the microfluid can be detected based on changes of capacitance of a capacitor in the detection circuit.

In some embodiments, the biosensor apparatus can detect the target molecule based on changes of electric potential of the micropore 41, when the target molecule is passing through the micropore 41.

Figure 4A:
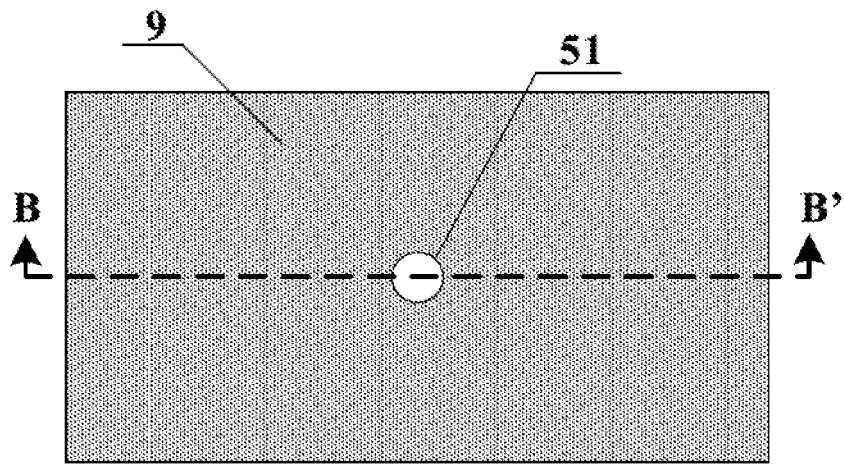
FIG. 4A is a plan view of a biosensor apparatus in some embodiments according to the present disclosure.
Figure 4B:
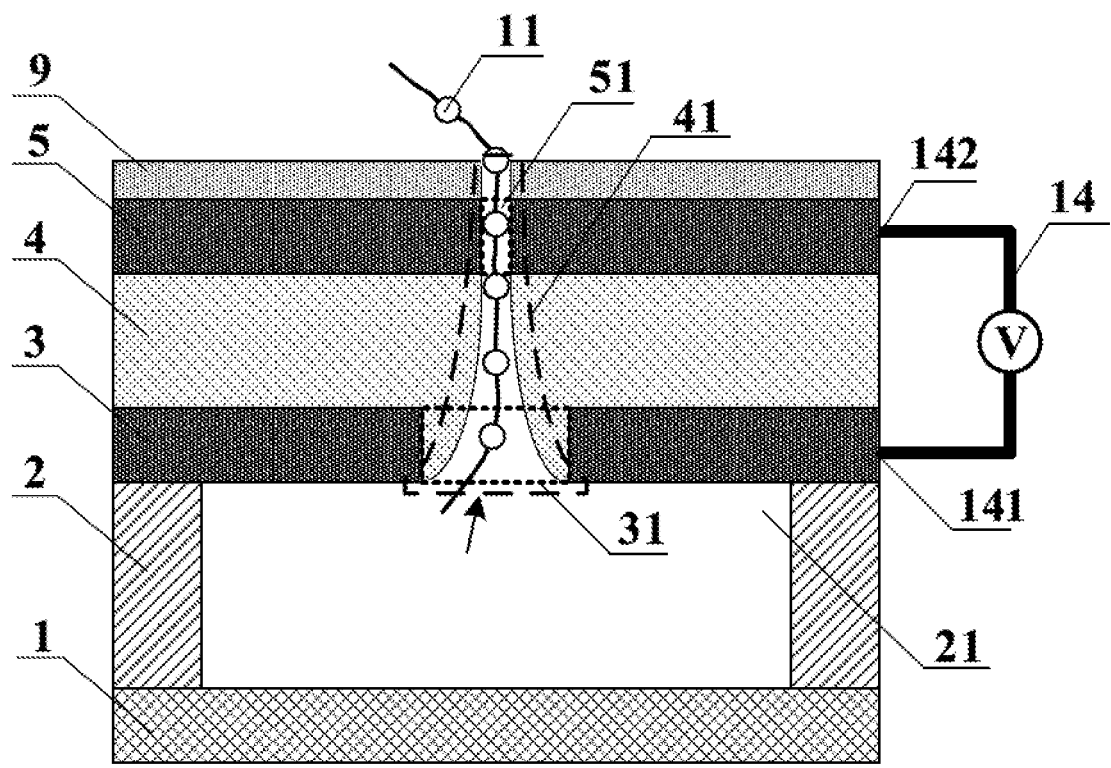
FIG. 4B is a cross-sectional view of a biosensor apparatus along an BB' direction in FIG. 4A.

FIG. 4A is a plan view of a biosensor apparatus in some embodiments according to the present disclosure. FIG. 4B is a cross-sectional view of a biosensor apparatus along an BB' direction in FIG. 4A. Referring to FIG. 4A and FIG. 4B, in some embodiments, the foundation layer 3 includes a conductive material; and the micropore layer 4 includes an insulating material. Optionally, the biosensor apparatus further includes a first conductive layer 5 on a side of the micropore layer 4 away from the base substrate 1.

Optionally, the foundation layer 3 is a first electrode of the biosensor apparatus; the first conductive layer 5 is a second electrode of the biosensor apparatus. Optionally, the first electrode connection terminal 141 of the detection circuit 14 is electrically connected to the first electrode (e.g. foundation layer 3) of the biosensor apparatus; the second electrode connection terminal 142 of the detection circuit 14 is electrically connected to the second electrode (e.g. first conductive layer 5) of the biosensor apparatus. Optionally, the detection circuit 14 includes a power source. So, by electrically connected with the biosensor apparatus, the detection circuit 14 can detect the target molecules based on a change of electric potential of the micropore 41.

Referring to FIG. 4A and FIG. 4B, in some embodiments, the first conductive layer 5 is a unitary electrode. Optionally, a first conductive layer throughhole 51 extends through the first conductive layer 5 to connect to the micropore 41.

Figure 5A:
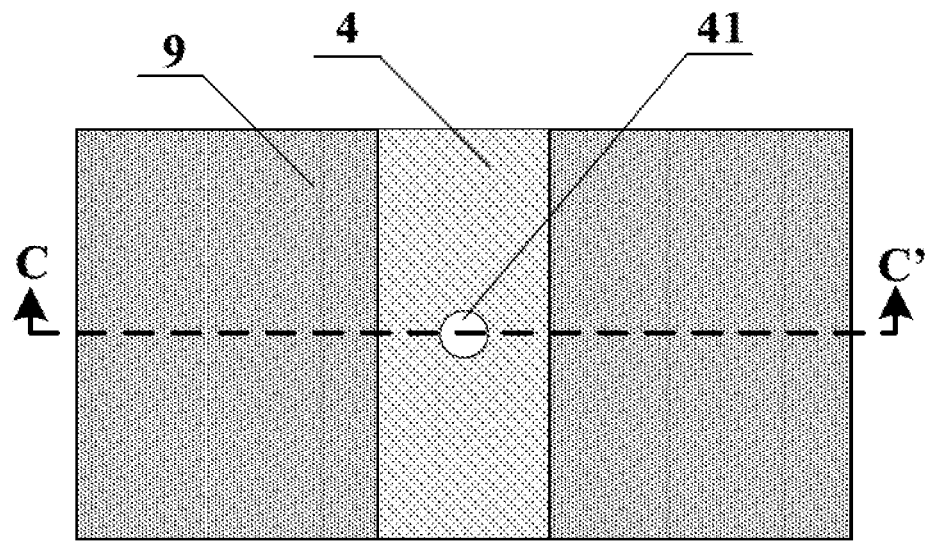
FIG. 5A is a plan view of a biosensor apparatus in some embodiments according to the present disclosure.
Figure 5B:
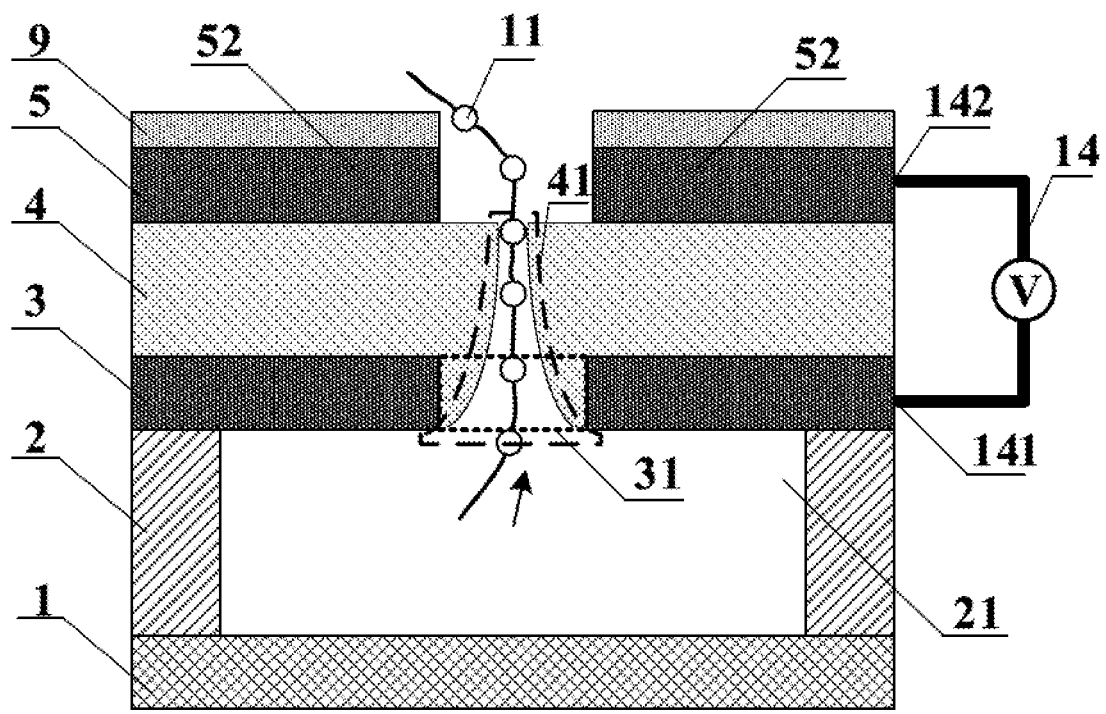
FIG. 5B is a cross-sectional view of a biosensor apparatus along an CC' direction in FIG. 5A.

FIG. 5A is a plan view of a biosensor apparatus in some embodiments according to the present disclosure. FIG. 5B is a cross-sectional view of a biosensor apparatus along an CC' direction in FIG. 5A. Referring to FIG. 5A and FIG. 5B, in some embodiments, the first conductive layer 5 includes two first block electrodes 52 spaced apart from each other and on two opposite side of a periphery of the micropore 41. For example, the two first block electrodes 52 are both block electrodes. Optionally, the two first block electrodes 52 are insulated from each other.

Optionally, the two first block electrodes 52 have a same electric potential, and a same polarity. Optionally, the two first block electrodes 52 perform not only the detection function, but also microfluid control function. For example, by adjusting the electric potentials of the two first block electrodes 52, a movement of the microfluid having the target molecules 11 can be adjusted. So, the two first block electrodes 52 can be configured to control the microfluid having the target molecules 11 to move faster by controlling the electric potentials of the two first block electrodes 52, resulting in a more controllable and more accurate detection process.

In some embodiments, referring to FIG. 1, FIG. 4B, and FIG. 5B, the biosensor apparatus is disposed in the detection system described herein to detect the target molecule 11. In one example, the driving controller 13 in the detection system drives the microfluid having the target molecule 13 to the first fluid channel 21, and drives the microfluid having the target molecule 11 to pass through the micropore 41. In another example, the driving controller 13 in the detection system drives the microfluid having the target molecule 11 to pass through the micropore 41, then enter the first fluid channel 21, and flow out of the biosensor apparatus.

Optionally, the detection circuit 14 includes a voltmeter. A power source of the voltmeter is the power source of the detection circuit 14. The first electrode connection terminal 141 of the detection circuit 14 is electrically connected to the foundation layer 3. The second electrode connection terminal 142 of the detection circuit 14 is electrically connected to the first conductive layer 5.

When the target molecule 11 is passing through the micropore 41, charges carried by the target molecule 11 may cause a change of charges on a capacitor formed between the first conductive layer 5 and the foundation layer 3. The charges carried by the target molecule 11 may also cause a change of a potential difference between the first conductive layer 5 and the foundation layer 3.

Optionally, different target molecules passing through the micropore 41 cause different changes of the potential difference between the first conductive layer 5 and the foundation layer 3. By analyzing different changes of the potential difference between the first conductive layer 5 and the foundation layer 3, the different target molecules passing through the micropore 41 can be defected by the detection circuit 14.

Figure 6A:
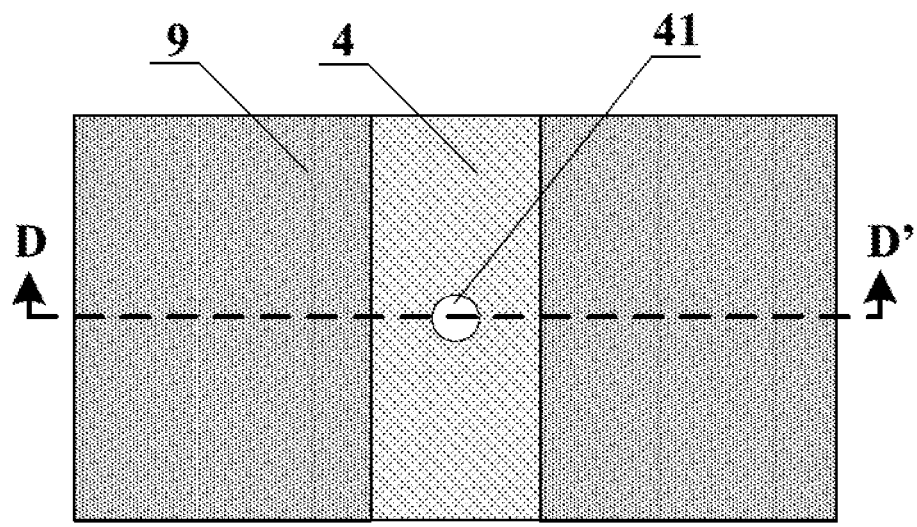
FIG. 6A is a plan view of a biosensor apparatus in some embodiments according to the present disclosure.
Figure 6B:
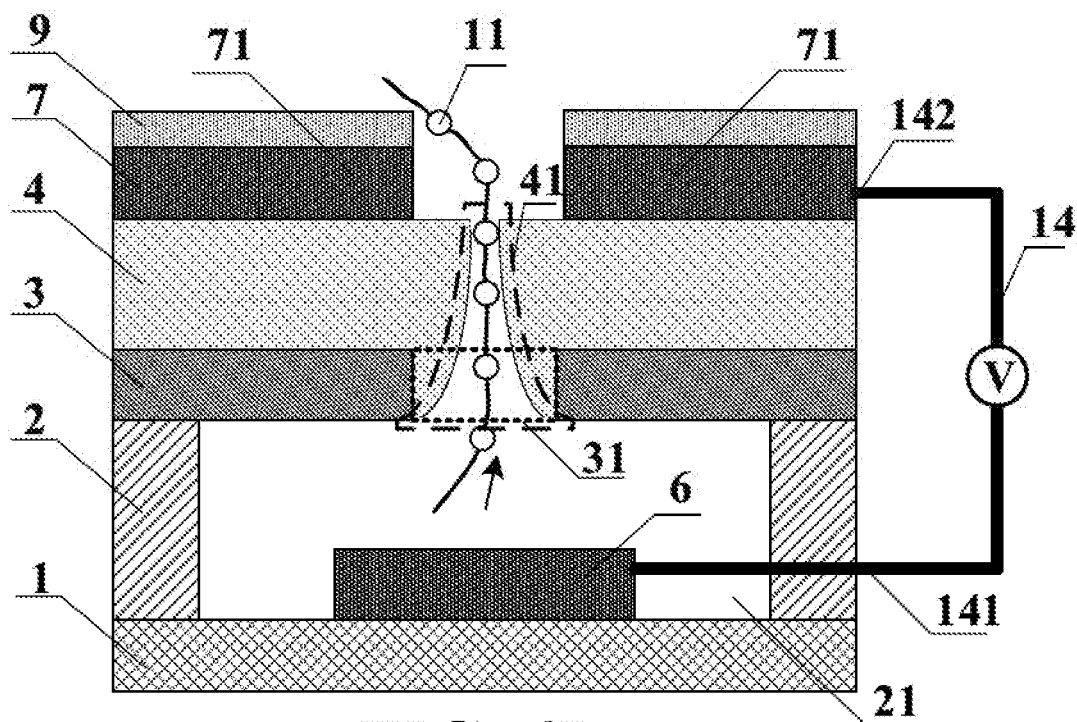
FIG. 6B is a cross-sectional view of a biosensor apparatus along an DD' direction in FIG. 6A.

FIG. 6A is a plan view of a biosensor apparatus in some embodiments according to the present disclosure. FIG. 6B is a cross-sectional view of a biosensor apparatus along an DD' direction in FIG. 6A. Referring to FIG. 6A and FIG. 6B, in some embodiments, the foundation layer 3 includes an insulating material; the micropore layer 4 includes an insulating material. Optionally, the biosensor apparatus further includes a detection electrode 6 in the first fluid channel 21; and a second conductive layer 7 on a side of the micropore layer 4 away from the base substrate 1. For example, the detection electrode 6 is on the base substrate 1.

Referring to FIG. 6A and FIG. 6B, in some embodiments, the second conductive layer 7 includes two second block electrodes 71 spaced apart from each other and on two opposite side of a periphery of the micropore 41. For example, the two second block electrodes 71 are both block electrodes. Optionally, the two second block electrodes 71 are insulated from each other. So, there are several electrodes disposed in a surrounding area of the micropore 41, the several electrodes includes the two second block electrodes 71, and the detection electrode 6. A combination of electrodes selected from a group consisting of the two second block electrodes 71, and the detection electrode 6 may perform different functions.

Optionally, by using one of the two second block electrodes 71 and the detection electrode 6, the microfluid having the target molecule 11 can be driven to pass through the first fluid channel 21 and the micropore 41, to allow the detection circuit 14 to detect the target molecule 11.

Optionally, the two second block electrodes 71 have a same electric potential. Optionally, the two second block electrodes 71 perform not only the detection function, but also a function of controlling microfluid. For example, by adjusting the electric potentials of the two second block electrodes 71, a movement of the microfluid having the target molecules 11 can be controlled. So, the two second block electrodes 71 can be configured to control the microfluid having the target molecules 11 to move faster by controlling the electric potentials of the two second block electrodes 71, resulting in a more controllable and more accurate detection process.

In some embodiments, referring to FIG. 1 and FIG. 6B, the biosensor apparatus is disposed in the detection system described herein to detect the target molecule 11. In one example, the driving controller 13 in the detection system drives the microfluid having the target molecule 11 to the first fluid channel 21, and drives the microfluid having the target molecule 11 to pass through the micropore 41. In another example, the driving controller 13 in the detection system drives the microfluid having the target molecule 11 to pass through the micropore 41, then enter the first fluid channel 21 and flow out of the biosensor apparatus.

Optionally, the detection circuit 14 includes a voltmeter. A power source of the voltmeter is the power source of the detection circuit 14. The first electrode connection terminal 141 of the detection circuit 14 is electrically connected to the detection electrode 6. The second electrode connection terminal 142 of the detection circuit 14 is electrically connected to the second conductive layer 7.

When the target molecule 11 is passing through the micropore 41, charges carried by the target molecule 11 may cause a change of charges on a capacitor formed between the second conductive layer 7 and the detection electrode 6. The charges carried by the target molecule 11 may also cause a change of a potential difference between the second conductive layer 7 and the detection electrode 6.

Optionally, different target molecules passing through the micropore 41 cause different changes of the potential difference between the second conductive layer 7 and detection electrode 6. By analyzing different changes of the potential difference between the second conductive layer 7 and the detection electrode 6, the different target molecules passing through the micropore 41 can be detected by the detection circuit 14.

In some embodiments, referring to FIG. 1, the biosensor apparatus can detect the target molecule, when the target is passing through the micropore 41, based on changes of current of the micropore 41. Optionally, the changes of current of the micropore 41 include a change of current horizontally passing though the micropore 41. Optionally, the changes of current of the micropore 41 include a change of current vertically passing though the micropore 41.

Figure 7A:
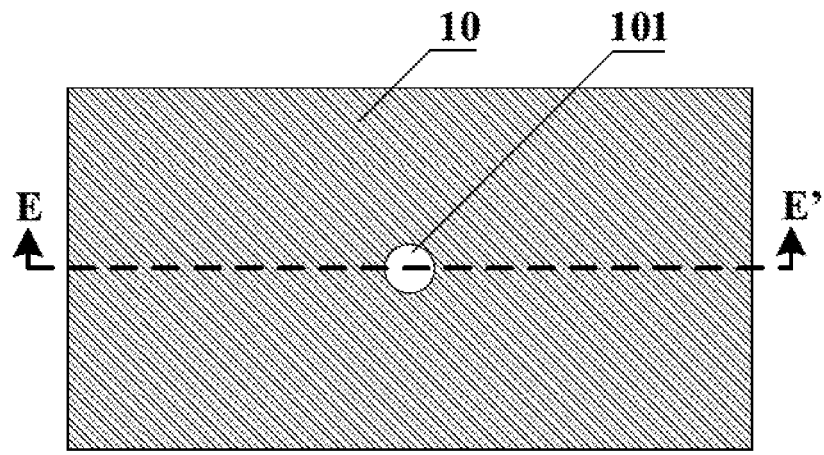
FIG. 7A is a plan view of a biosensor apparatus in some embodiments according to the present disclosure.
Figure 7B:
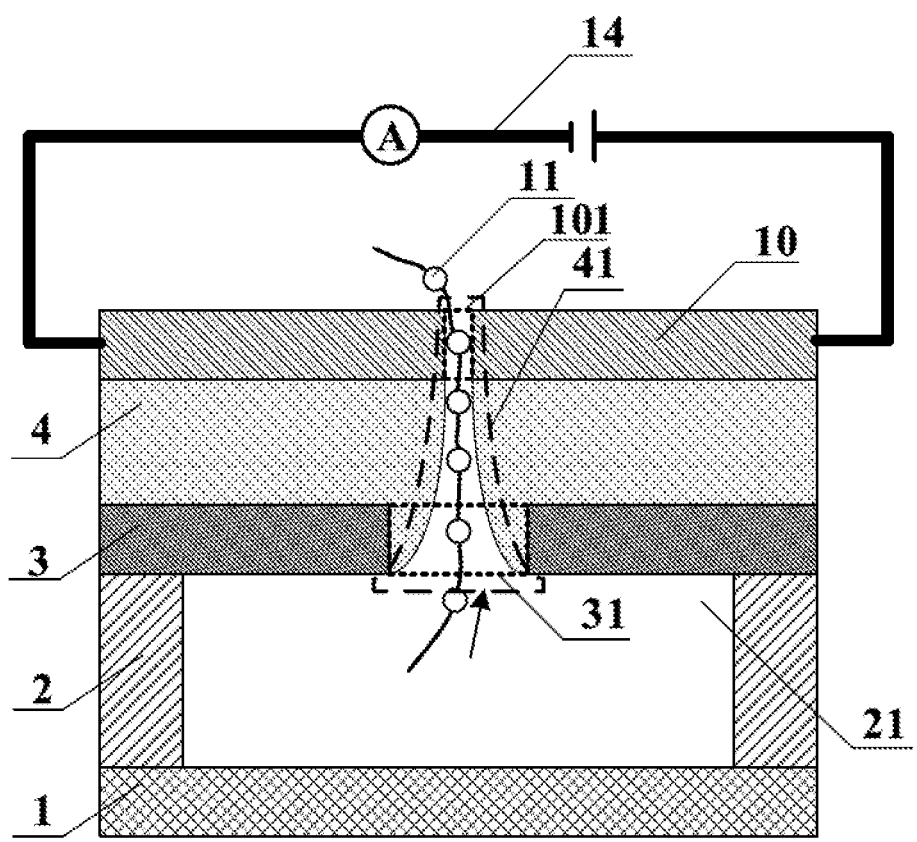
FIG. 7B is a cross-sectional view of a biosensor apparatus along an EE' direction in FIG. 7A.

FIG. 7A is a plan view of a biosensor apparatus in some embodiments according to the present disclosure. FIG. 7B is a cross-sectional view of a biosensor apparatus along an EE' direction in FIG. 7A. Referring to FIG. 7A and FIG. 7B, in some embodiments, the foundation layer 3 includes an insulating material; the micropore layer 4 includes an insulating material. Optionally, the biosensor apparatus further includes a semiconductor layer 10 on a side of the micropore layer 4 away from the base substrate 1. Optionally, a semiconductor layer throughhole 101 extends through the semiconductor layer 10 to connect to the micropore 41.

Optionally, the semiconductor layer 10 is formed on the side of the micropore layer 4, because the micropore layer 4 includes the micropore 41, the semiconductor layer 10 formed on the micropore layer 4 naturally has a semiconductor layer throughhole 101 connected to the micropore 41. In one example, the semiconductor layer throughhole 101 has a diameter substantially equivalent to the diameter of the micropore 41. In another example, the semiconductor layer throughhole 101 has a minimum diameter substantially equivalent to the minimum diameter of the micropore 41.

In some embodiments, referring to FIG. 1 and FIG. 7B, the biosensor apparatus is disposed in the detection system described herein to detect the target molecule 11. In one example, the driving controller 13 in the detection system drives the microfluid having the target molecule 11 to the first fluid channel 21, and drives the microfluid having the target molecule 11 to pass through the micropore 41. In another example, the driving controller 13 in the detection system drives the microfluid having the target molecule 11 to pass through the micropore 41, then enter the first fluid channel 21, and flow out of the biosensor apparatus.

Optionally, the semiconductor layer 10 is electrically connected to the detection circuit 14. Optionally, the detection circuit 14 includes a power source and an ammeter.

When the target molecule 11 is passing through the micropore 41, a resistance of the detection circuit 14 changes, and a current of the detection circuit 14 changes based on a change of the resistance of the detection circuit 14. A change of current of the detection circuit 14 can be measured by the ammeter in the detection circuit 14.

Optionally, different target molecules passing through the micropore 41 cause different changes of the current in the detection circuit 14. By analyzing different changes of the current in the detection circuit 14, the different target molecules passing through the micropore 41 can be detected by the detection circuit 14.

Figure 8A:
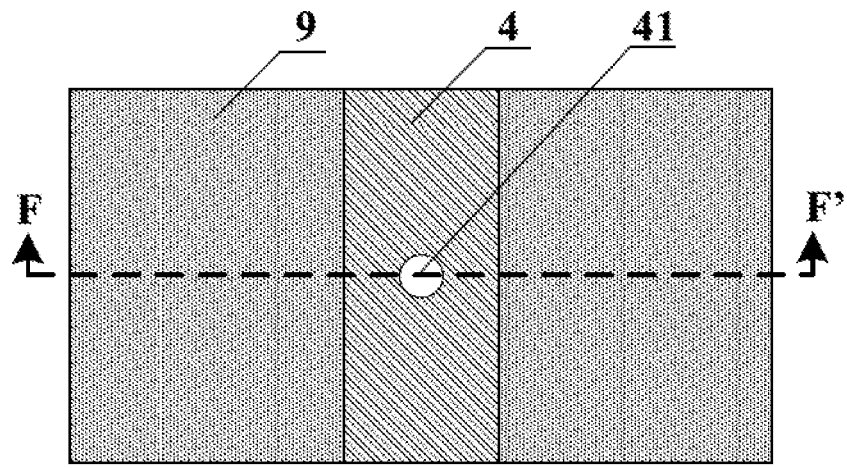
FIG. 8A is a plan view of a biosensor apparatus in some embodiments according to the present disclosure.
Figure 8B:
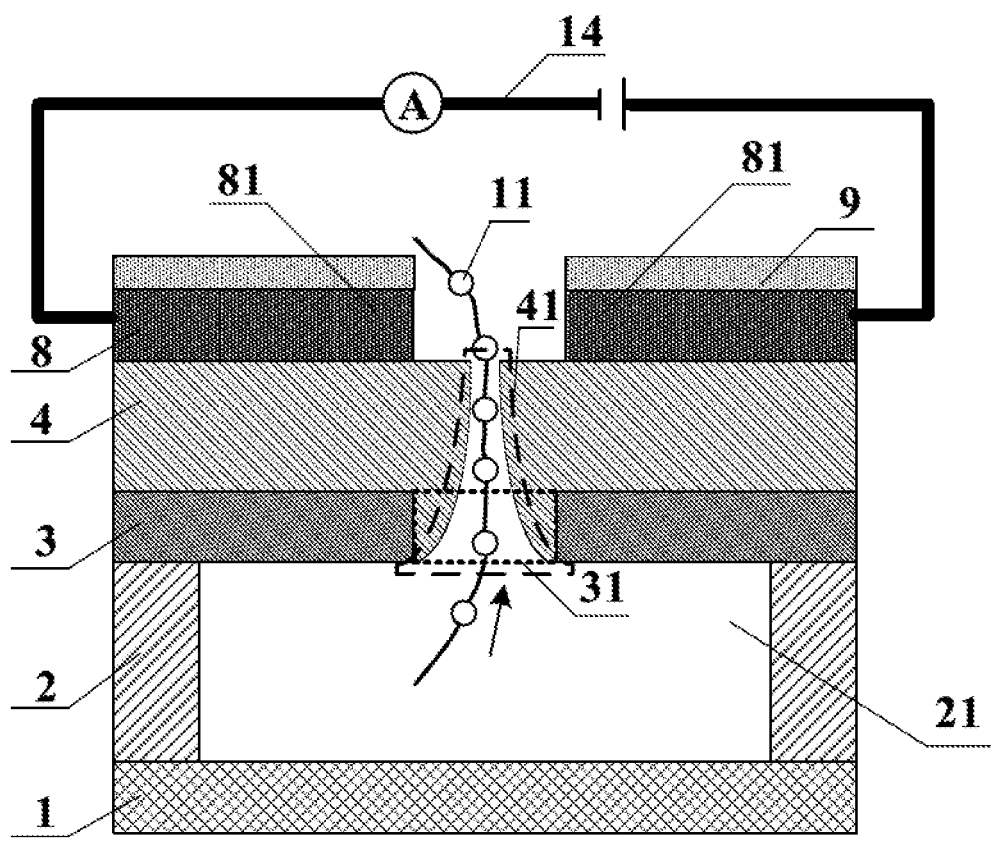
FIG. 8B is a cross-sectional view of a biosensor apparatus along an FF' direction in FIG. 8A.

FIG. 8A is a plan view of a biosensor apparatus in some embodiments according to the present disclosure. FIG. 8B is a cross-sectional view of a biosensor apparatus along an FF' direction in FIG. 8A. Referring to both FIG. 8A and FIG. 8B, in some embodiments, the foundation layer 3 includes an insulating material; the micropore layer 4 includes a semiconductor material. Optionally, the biosensor apparatus further includes a third conductive layer 8 on a side of the micropore layer 4 away from the base substrate 1. Optionally, the third conductive layer 8 includes two third block electrodes 81 spaced apart from each other and on two opposite side of a periphery of the micropore 41. Optionally, the two third block electrodes 81 are two block electrodes. Optionally, the two third block electrodes 81 are insulated from each other.

In some embodiments, referring to FIG. 1 and FIG. 8B, the biosensor apparatus is disposed in the detection system described herein to detect the target molecule 11. In one example, the driving controller 13 in the detection system drives the microfluid having the target molecule 11 to the first fluid channel 21, and drives the microfluid having the target molecule 11 to pass through the micropore 41. In another example, the driving controller 13 in the detection system drives the microfluid having the target molecule 11 to pass through the micropore 41, then enter the first fluid channel 21, and flow out of the biosensor apparatus.

Optionally, the detection circuit 14 includes a power source and an ammeter. Optionally, the two third block electrodes 81 are respectively connected to the detection circuit 14.

In the detection circuit 14, because the micropore layer 4 include the semiconductor material, the micropore layer 4 is equivalent to adding a resistor in the detection circuit 14. A resistance of the semiconductor material of the micropore layer 4 is less than a resistance of the microfluid between the two third block electrodes 81. As a result, at least a portion of a current in the detection circuit 14 passes through the micropore layer 4.

When the target molecule 11 is passing through the micropore 41, a resistance of the detection circuit 14 changes due to a change of a resistance in the microfluid in the micropore 41 caused by the presence of the target molecule 11, and a current of the detection circuit 14 changes based on a change of the resistance of the detection circuit 14. A change of current of the detection circuit 14 can be measured by the ammeter in the detection circuit 14.

Optionally, different target molecules passing through the micropore 41 cause different changes of the current in the detection circuit 14. By analyzing different changes of the current in the detection circuit 14, the different target molecules passing through the micropore 41 can be detected by the detection circuit 14.

Figure 9A:
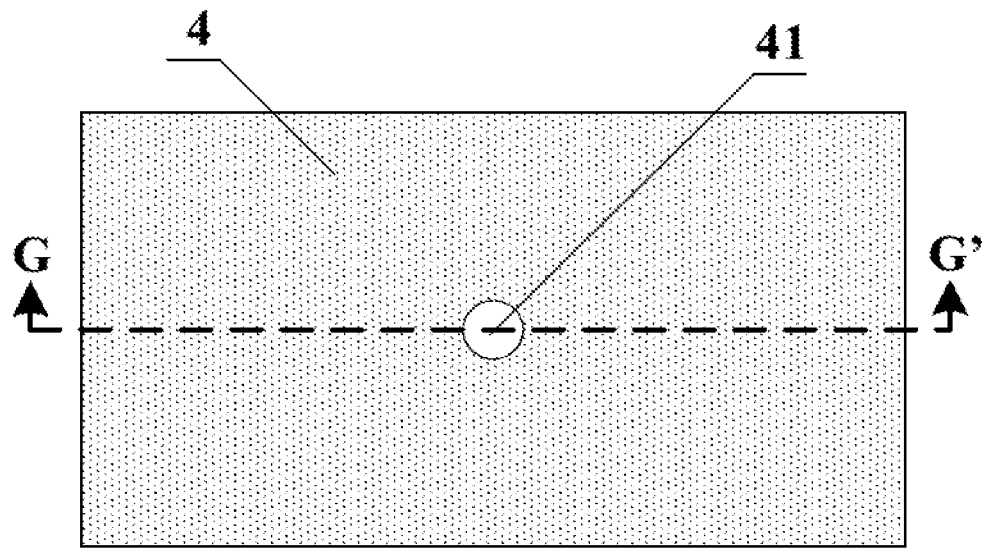
FIG. 9A is a plan view of a biosensor apparatus in some embodiments according to the present disclosure.
Figure 9B:
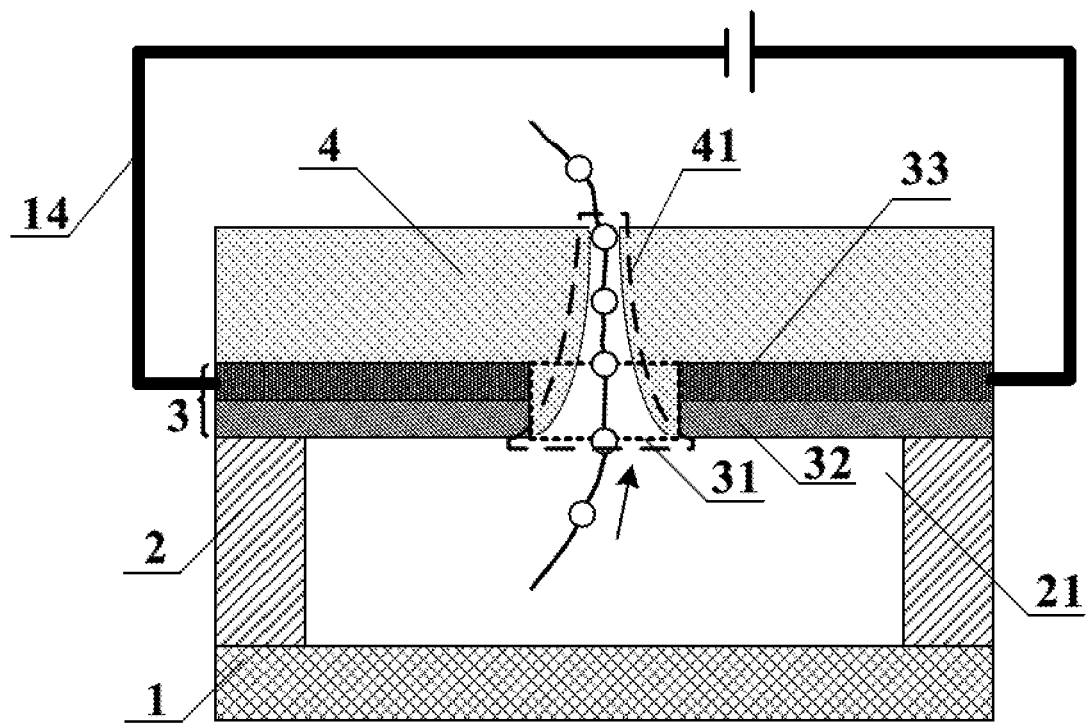
FIG. 9B is a cross-sectional view of a biosensor apparatus along an GG' direction in FIG. 9A.
Figure 9C:
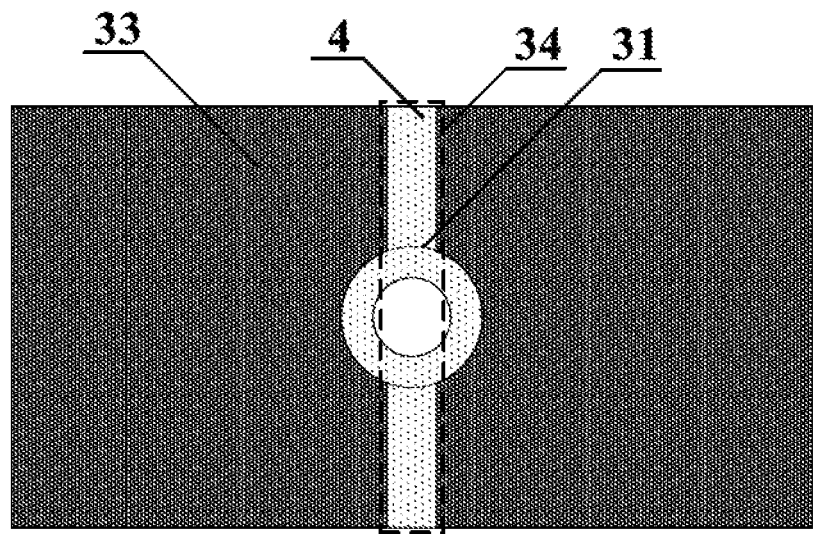
FIG. 9C is a plan view of a second foundation sub-layer in some embodiments according to the present disclosure.

FIG. 9A is a plan view of a biosensor apparatus in some embodiments according to the present disclosure. FIG. 9B is a cross-sectional view of a biosensor apparatus along an GG' direction in FIG. 9A. FIG. 9C is a plan view of a second foundation sub-layer in some embodiments according to the present disclosure. Referring to FIG. 9A, FIG. 9B, and FIG. 9C, in some embodiments, when the target molecule is passing through the micropore 41, the biosensor apparatus detects the target molecules 11 based on a change of capacitance of the micropore 41.

In some embodiments, the foundation layer 3 includes an insulating sub-layer 32 on a side of the first fluid channel layer 2 away from the base substrate 1, a conductive sub-layer 33 on a side of fee insulating sub-layer 32 away from fee base substrate 1. Optionally, the insulating sub-layer 32 includes an insulating material; and fee conductive sub-layer 33 includes a conductive material. Optionally, fee foundation layer 3 is divided into two parts spaced apart from each other by the foundation layer throughhole 33 and a split gap 34 connected to the foundation layer throughhole 31. Optionally, the micropore layer 4 extends into the split gap 34 and fills in the split gap 34.

Optionally, the conductive sub-layer 33 is also separated into two parts by the foundation layer throughhole 31 and the split gap 34. Optionally, the two parts of the conductive sub-layer 33 are insulated from each other by the micropore layer 4 and the insulating sub-layer 32, because the micropore layer 4 extends into the split gaps 34 and substantially covers edges of the two parts of the conductive sub-layer 33 closer to the micropore 41, and the insulating sub-layer 32 covers a surface of the conductive sub-layer 33 closer to the base substrate 1. Moreover, the orthographic projection of the conductive sub-layer 33 on the base substrate 1 is substantially covered by the orthographic projection of the insulating sub-layer 32 on the base substrate 1.

Optionally, in a region surrounding the micropore 41, an orthographic projection of the micropore layer 4 on the base substrate 1 substantially covers an orthographic projection of the foundation layer 3 on the base substrate 1. In one example, the orthographic projection of the micropore layer 4 on the base substrate 1 substantially covers an orthographic projection of the insulating sub-layer 32 on the base substrate 1. In another example, the orthographic projection of the micropore layer 4 on the base substrate 1 substantially covers an orthographic projection of the conductive sub-layer 33 on the base substrate 1.

In some embodiments, referring to FIG. 1 and FIG. 9B, the biosensor apparatus is disposed in the detection system described herein to detect the target molecule 11. In one example, the driving controller 13 in the detection system drives the microfluid having the target molecule 11 to the first fluid channel 21, and drives the microfluid having the target molecule 11 to pass through the micropore 41. In another example, the driving controller 13 in the detection system drives the microfluid having the target molecule 11 to pass through the micropore 41, then enter the first fluid channel 21, and flow out of the biosensor apparatus.

Optionally, the detection circuit 14 includes a power source. Optionally, the two parts of the conductive sub-layer 33 are respectively connected to the detection circuit 14. Optionally, a capacitor is formed between the two separated parts of the conductive sub-layer 33.

When the target molecule 11 is passing through the micropore 41, charges of the target molecule 11 causes a change of charges in the surface of the micropore 41, resulting in a change of the capacitor formed between the two separated parts of the conductive sub-layer 33. A capacitance measuring device is used to measure a change of capacitance of the capacitor formed between the two separated parts of the conductive sub-layer 33.

Optionally, different target molecules passing through the micropore 41 cause different changes of the capacitance of the capacitor formed between the two separated part of the conductive sub-layer 33. By analyzing different changes of the current in the detection circuit 14, the different target molecules passing through the micropore 41 can be detected by the detection circuit 14.

In some embodiments, referring to FIG. 4B, FIG. 5B, FIG. 6B, and FIG. 8B, the biosensor apparatus further includes a capping layer 9 covering an outmost conductive layer of the biosensor apparatus, which may prevent the outmost conductive layer from being exposing to air.

In one example, referring to FIG. 4B, the outmost conductive layer of the biosensor apparatus is the first conductive layer 5, and the capping layer 9 is formed on a side of the first conductive layer 5 away from the base substrate 1 to protect the first conductive layer 5.

In another example, referring to FIG. 5B, the outmost conductive layer of the biosensor apparatus is the first conductive layer 5, and the capping layer 9 is formed on a side of the first conductive layer 5 away from the base substrate 1 to protect the first conductive layer 5.

In another example, referring to FIG. 6B, the outmost conductive layer of the biosensor apparatus is the second conductive layer 7, and the capping layer 9 is formed on a side of the second conductive layer 7 away from the base substrate 1 to protect the second conductive layer 7.

In another example, referring to FIG. 8B, the outmost conductive layer of the biosensor apparatus is the third conductive layer 8, and the capping layer 9 is formed on a side of the third conductive layer 8 away from the base substrate 1 to protect the third conductive layer 8.

In some embodiments, the biosensor apparatus is connected to a chip or a sensor to form a detection chip or detection sensor. For example, the detection chip or detection sensor may have multi-functions including, but not limited to, detecting the target molecules.

In another aspect, the present disclosure also provides a method of fabricating a biosensor apparatus. FIGS. 10A-10D are schematic diagrams illustrating a method of fabricating a biosensor apparatus in some embodiments according to present disclosure. Referring to FIGS. 10A-10D, in some embodiments, the method of fabricating a biosensor apparatus includes forming a first fluid channel layer 2 on the base substrate 1; and forming a foundation layer 3 on a side of the first fluid channel layer 2 away from the base substrate 1.

Optionally, prior to forming the first fluid channel layer 2 and the foundation layer 3, the method of fabricating a biosensor apparatus further includes cleaning the base substrate 1.

Figure 10A:
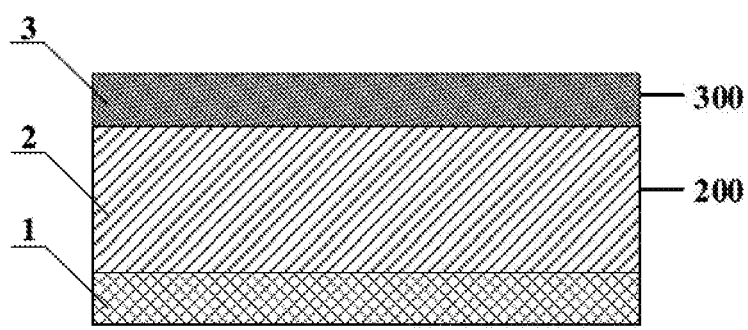
FIGS. 10A-10D are schematic diagrams illustrating a method of fabricating a biosensor apparatus in some embodiments according to present disclosure.
Figure 10B:
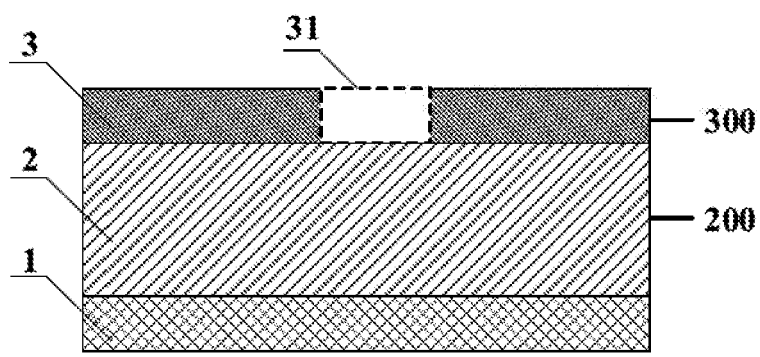
Figure 10C:
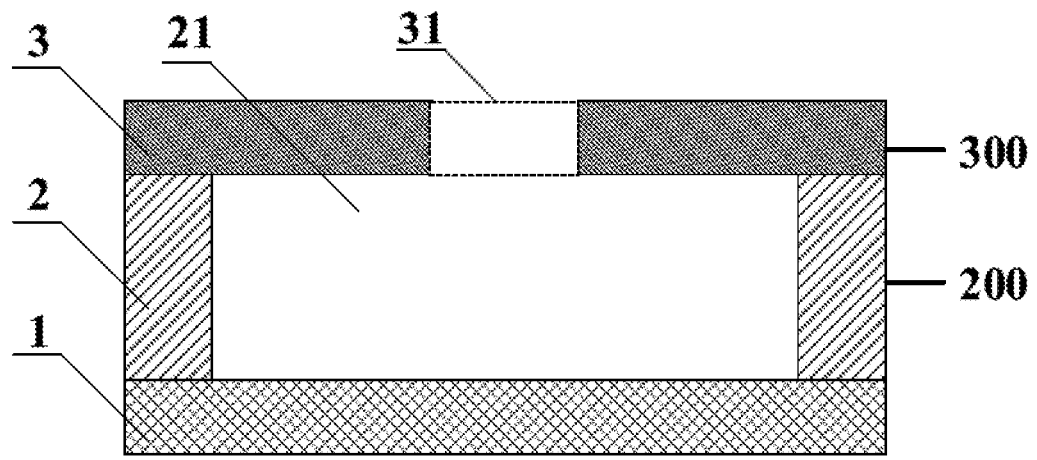

In some embodiments, referring to FIG. 10A, FIG. 10B, and FIG. 10C, forming the first fluid channel layer 2 and forming the foundation layer 3 includes forming a first fluid channel material layer 200 on a base substrate 1; forming a foundation material layer 300 on a side of the first fluid channel material layer 200 away from the base substrate 1; patterning the foundation material layer 300 to form the foundation layer 3, the foundation layer 30 formed to have the foundation layer throughhole 31 extending therethrough; and patterning the first fluid channel material layer 200 to form the first fluid channel layer 2, the first fluid channel layer 2 formed to have the first fluid channel 21 passing therethrough. Optionally, the foundation layer throughhole 31 is formed to connect to the first fluid channel 21.

Optionally, the foundation layer throughhole 31 is formed by etching the foundation material layer 300. For example, the foundation layer throughhole 31 is formed by using lithography.

Optionally, the first fluid channel 21 is formed by etching the first fluid channel material layer 200. Various appropriate methods may be used for forming the first fluid channel 21. Examples of methods suitable for forming the first fluid channel 21 include, but are not limited to over etching, undercutting, and dissolving. In one example, "undercutting" refers to an etching process to form the first fluid channel 21 having a small opening in a plane having the side of the first fluid channel layer 2 away from the base substrate 1, and having a bigger opening in a plane having the side of the first fluid channel layer 2 closer to the base substrate 1. In another example, "undercutting" refers to an etching process of forming the first fluid channel 21 having irregular shape extending through the first fluid channel layer 2. In another example, "dissolving" refers to a process applying a corrosion solution to the first fluid channel layer 2 to form the first fluid channel 21. The corrosion solution erodes only the first fluid channel 21. It won't erode layers in direct contact with the first fluid channel material layer 200, e.g. the base substrate 1 and the foundation layer 3.

Figure 10D:
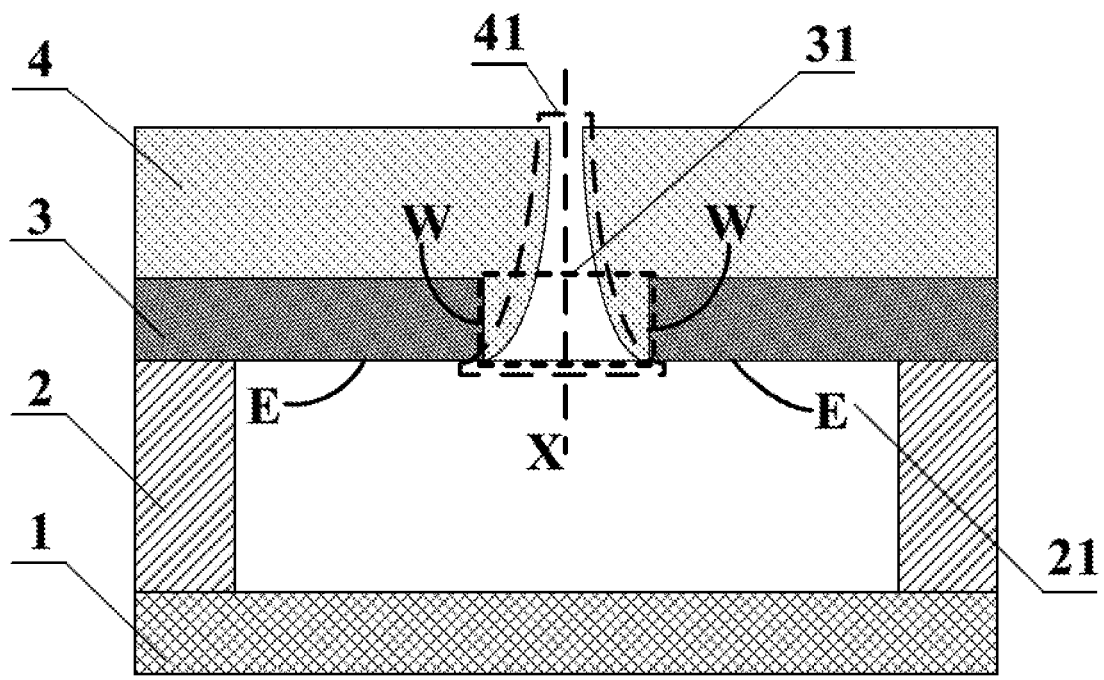

Referring to FIG. 10D, the method of fabricating a biosensor apparatus further includes forming a micropore layer 4 on a side of the foundation layer 3 away from the base substrate 1. Optionally, forming the micropore layer 4 includes depositing a micropore layer material on a side of the foundation layer 3 away from the base substrate 1. Optionally, the micropore layer material is deposited onto an inner wall W of the foundation layer throughhole 31.

Optionally, a micropore is formed to extend through the micropore layer 4 to connect to the first fluid channel 21 through the foundation layer throughhole 31. Optionally, the micropore layer 4 is formed to extend into the foundation layer throughhole 31 and at least partially covers an inner wall W of the foundation layer throughhole 31.

Optionally, the micropore layer 4 is formed by depositing micropore layer material to the foundation layer 3. Various depositing methods may be used for depositing the micropore layer 4. Examples of appropriate depositing methods include, but are not limited to, physical vapor depositions, and chemical vapor depositions. Optionally, the physical vapor depositions include sputtering depositions. Optionally, the chemical vapor depositions include plasma enhanced chemical vapor depositions and atomic layer depositions.

Various appropriate materials may be used for depositing the micropore layer 4. Examples of materials may be used for depositing the micropore layer 4 include, but are not limited to, insulating materials, semiconductor materials, conductive materials, and combinations of materials selected from a group consisting of insulating materials, semiconductor materials, conductive materials. By using various types of materials to form the micropore layer 4, the biosensor apparatus may have different functions.

Optionally, the micropore layer 4 and the micropore 41 is formed using deposition process instead of etching process. When different materials is used to form the micropore layer 4 and the micropore 41 using deposition processes, it is not necessary to use different etching processes for different materials forming the micropore layer 4.

Optionally, in a region surrounding the micropore 41, an orthographic projection of the micropore layer 4 on the base substrate 1 substantially covers an orthographic projection of the foundation layer 3 on the base substrate 1.

Optionally, a diameter of the micropore 41 gradually increases from a narrowest point of the micropore 41 to an outer edge E of the foundation layer 3 throughhole, along a direction from the micropore layer 4 toward the base substrate 1.

Optionally, in the process of depositing the micropore layer 4 on the foundation layer 3 to form the micropore 41, the micropore 41 is naturally formed when the micropore layer 4 is deposited on the foundation layer 3. By controlling parameters in the deposition process, the lateral deposition growth rate of the micropore layer material can be controlled and the diameters of the micropore 41 can be controlled.

For example, by controlling parameters in the deposition process, the micropore layer material can be deposited on the inner wall W of the foundation layer throughhole 31, and micropore layer material continuously grows horizontally toward a center axis X of the foundation layer throughhole 31 to form a pore. During the deposition process, a diameter of a cross section of the pore parallel to the base substrate 1 gradually shrinks to form the micropore 41.

Optionally, forming the foundation layer throughhole 31 requires a low accuracy. Forming the micropore 41 is affected by the shape of the foundation layer throughhole 31, the parameters of the deposition process, and the materials used for deposition. It is not necessary to use devices including electron beam exposure devices and precision etching devices to form the micropore 41. Low accuracy devices for forming the foundation layer throughhole 31 and deposition processes for forming the micropore 41 are sufficient in the process of fabricating the biosensor apparatus, and using low accuracy devices and deposition processes may lower the cost of fabricating the biosensor apparatus, and make the mass production of the biosensor apparatus possible. The method described herein to fabricate the biosensor apparatus can form high uniform biosensor apparatus.

Figure 11:
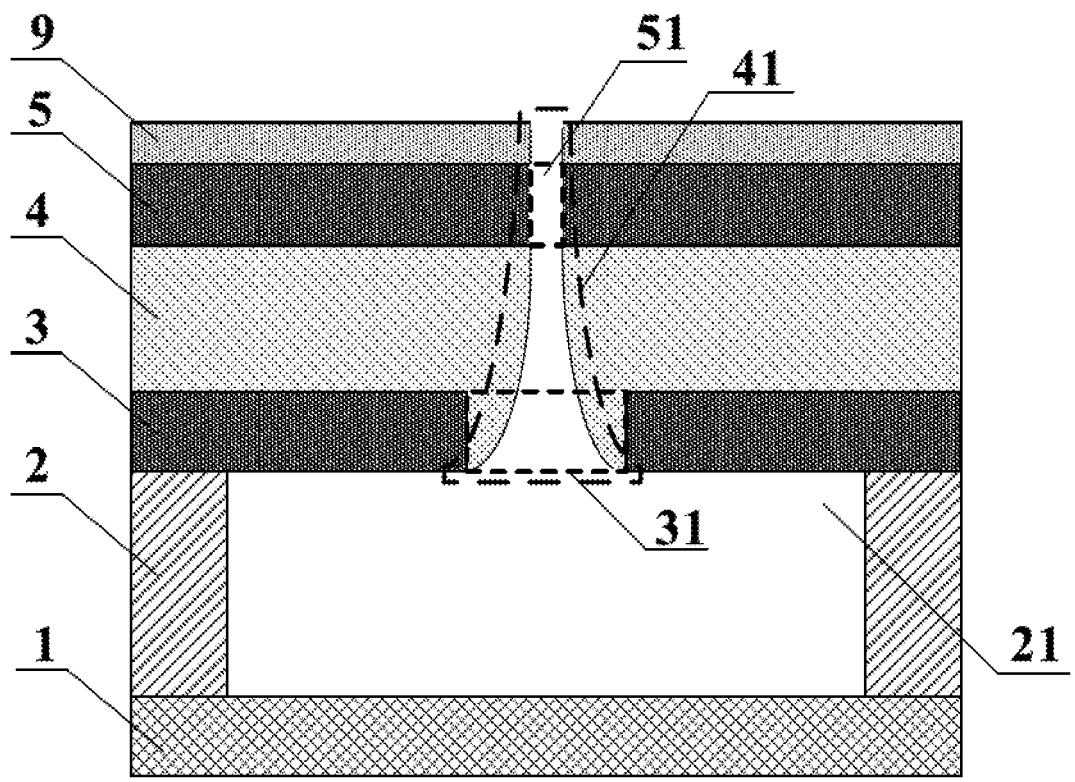
FIG. 11 is a schematic diagram illustrating a method of fabricating a biosensor apparatus in some embodiments according to present disclosure.

FIG. 11 is a schematic diagram illustrating a method of fabricating a biosensor apparatus in some embodiments according to present disclosure. Referring to FIG. 11, in some embodiments, the foundation layer 3 is formed using a conductive material; and the micropore layer 4 is formed using an insulating material. Optionally, the method further includes, subsequent to forming the micropore layer 4, forming a first conductive layer 5 on a side of the micropore layer 4 away from the base substrate 1.

Optionally, the foundation layer 3 is a first electrode of the biosensor apparatus; the first conductive layer 5 is a second electrode of the biosensor apparatus. Optionally, a power source is connected to the second electrode (e.g. the first conductive layer 5) of the biosensor apparatus.

FIGS. 12A-12E are schematic diagrams illustrating a method of fabricating a biosensor apparatus in some embodiments according to present disclosure. Referring to FIGS. 12A-12E, in some embodiments, the foundation layer 3 is formed using an insulating material; and the micropore layer 4 is formed using an insulating material.

Optionally, the method further includes prior to forming the first fluid channel layer 2, forming a detection electrode 6 on the base substrate 1; and subsequent to forming the micropore layer 4, forming a second conductive layer 7 on a side of the micropore layer 4 away from the base substrate 1.

Figure 12A:
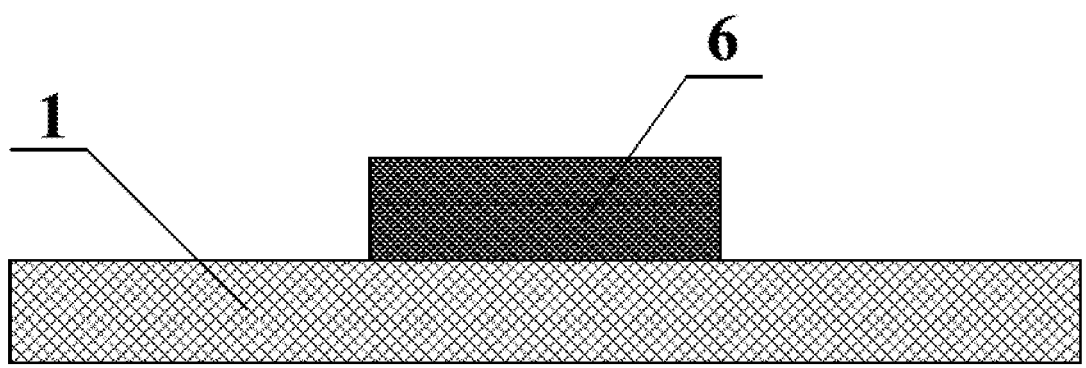
FIGS. 12A-12E are schematic diagrams illustrating a method of fabricating a biosensor apparatus in some embodiments according to present disclosure.
Figure 12B:
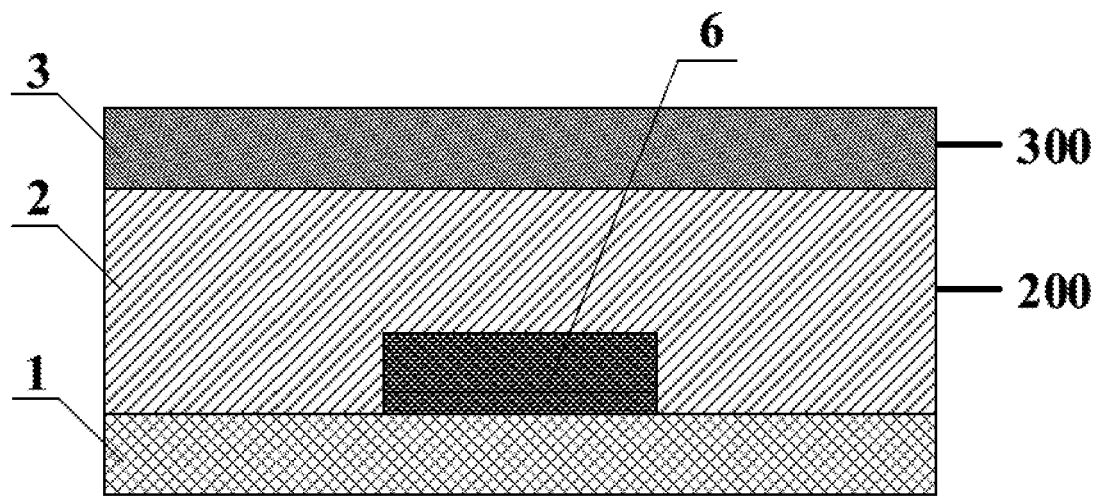

Referring to FIG. 12A, in some embodiments, the method includes forming the detection electrode 6 on the base substrate 1. Referring to FIG. 12B, the method includes forming the first fluid channel material layer 200 on a side of the detection electrode 6 away from the base substrate 1; and forming the foundation material layer 300 on a side of the first fluid channel material layer 200 away from the base substrate 1.

Figure 12C:
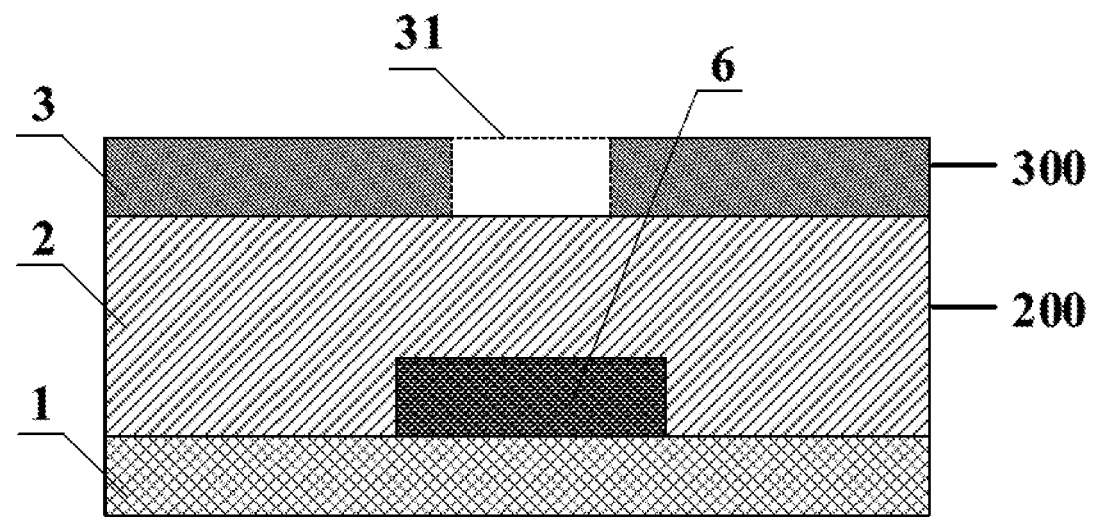

Referring to FIG. 12C, optionally, the method includes forming a foundation material layer 3 by patterning the foundation material layer 300. Optionally, the foundation layer 3 is formed to have the foundation layer throughhole 31 extending through the foundation layer 3.

Figure 12D:
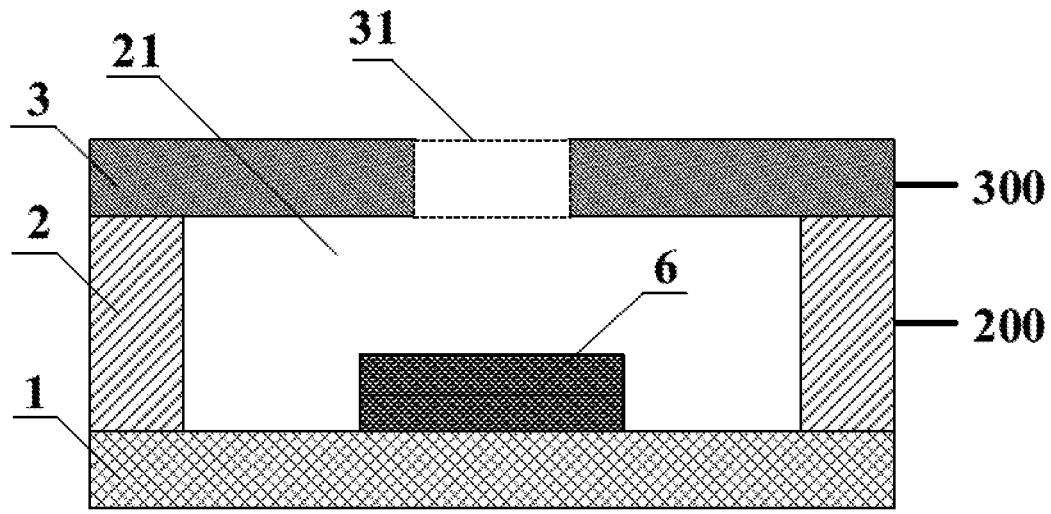

Referring to FIG. 12D, optionally, the method includes forming a first fluid channel layer 2 by patterning the first fluid channel material layer 200. Optionally, the first fluid channel layer 2 is formed to have the first fluid channel 21 passing through the first fluid channel layer 2. Optionally, the foundation layer throughhole 31 is formed to connect to the first fluid channel 21.

Figure 12E:
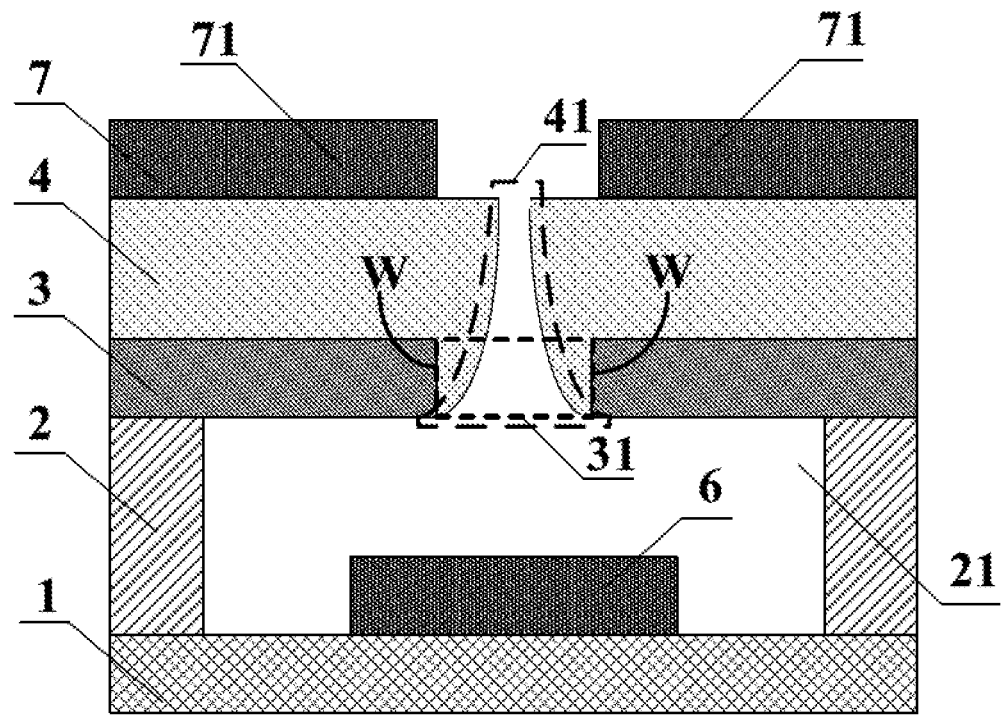

Referring to FIG. 12E, optionally, the method includes forming the micropore layer 4 on a side of the foundation layer 3 away from the base substrate 1; and forming a second conductive layer 7 on a side of the micropore layer 4 away from the base substrate 1. Optionally, forming the micropore layer 4 includes depositing a micropore layer material on a side of the foundation layer 3 away from the base substrate 1. Optionally, the micropore layer material is deposited onto an inner wall W of the foundation layer throughhole 31.

Optionally, the second conductive layer 7 is formed to include two second block electrodes 71 spaced apart from each other and on two opposite side of a periphery of the micropore 41. For example, the two second block electrodes 71 are both block electrodes. Optionally, the two second block electrodes 71 are insulated from each other. So, there are several electrodes disposed in a surrounding area of the micropore 41, the several electrodes includes the two second block electrodes 71, and the detection electrode 6. A plurality of electrodes may cooperate together to perform different functions.

Figure 13A:
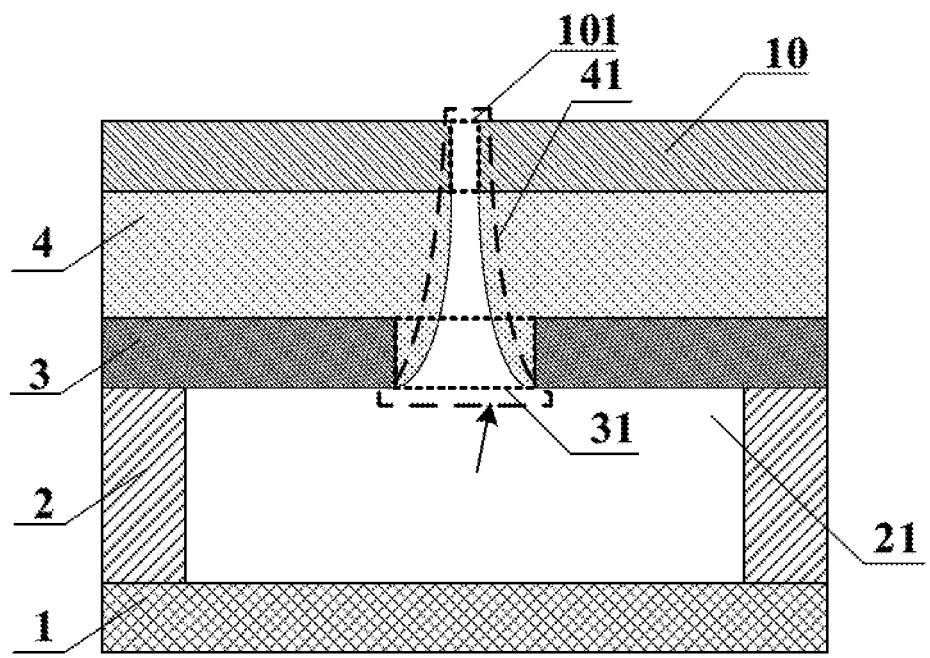
FIG. 13A is a schematic diagram illustrating a method of fabricating a biosensor apparatus in some embodiments according to present disclosure.

FIG. 13A is a schematic diagram illustrating a method of fabricating a biosensor apparatus in some embodiments according to present disclosure. Referring to FIG. 13A, the foundation layer 3 is formed using an insulating material; and the micropore layer 4 is formed using an insulating material. Optionally, the method further includes, subsequent to forming the micropore layer 4 in FIG. 10D, forming a semiconductor layer 10 on a side of the micropore layer 4 away from the base substrate 1. Optionally, a semiconductor layer throughhole 101 is formed to extend through the semiconductor layer 10 to connect to the micropore 41.

Figure 13B:
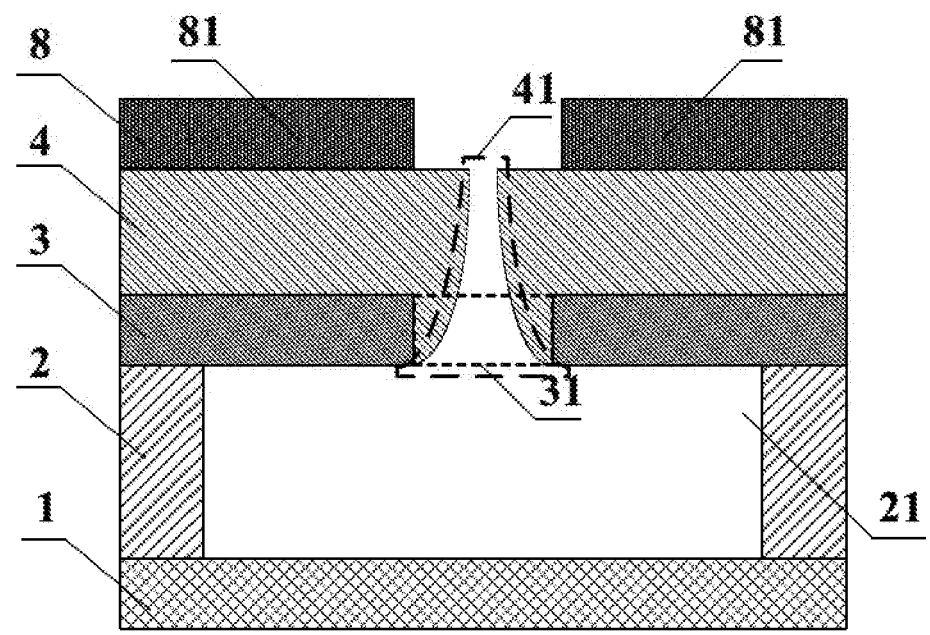
FIG. 13B is a schematic diagram illustrating a method of fabricating a biosensor apparatus in some embodiments according to present disclosure.

FIG. 13B is a schematic diagram illustrating a method of fabricating a biosensor apparatus in some embodiments according to present disclosure. Referring to FIG. 13B, the foundation layer 3 is formed using an insulating material; and the micropore layer 4 is formed using a semiconductor material. Optionally, die method further includes, subsequent to forming the micropore layer 4 in FIG. 10D, forming a third conductive layer 8 on a side of the micropore layer 4 away from the base substrate 1. Optionally, the third conductive layer 8 is formed to include two third block electrodes 81 spaced apart from each other and on two opposite side of a periphery of the micropore 41. Optionally, the two third block electrodes 81 are two block electrodes. Optionally, the two third block electrodes 81 are insulated from each other.

FIGS. 14A-14E are schematic diagrams illustrating a method of fabricating a biosensor apparatus in some embodiments according to present disclosure. Referring to FIGS. 14A-14E, in some embodiments, the method of fabricating a biosensor apparatus includes forming a first fluid channel layer 2 on the base substrate 1; and forming a foundation layer 3 on a side of the first fluid channel layer 2 away from the base substrate 1. Optionally, the foundation layer 3 include an insulating material and a conductive material. The micropore layer 4 includes an insulating material.

Figure 14A:
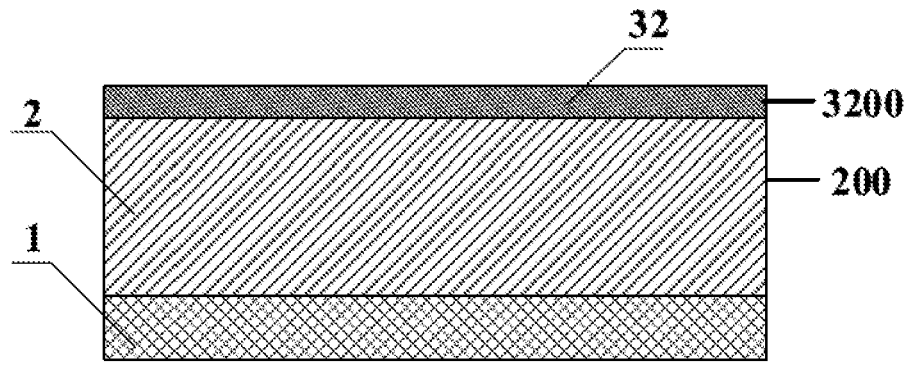
FIGS. 14A-14E are schematic diagrams illustrating a method of fabricating a biosensor apparatus in some embodiments according to present disclosure.
Figure 14B:
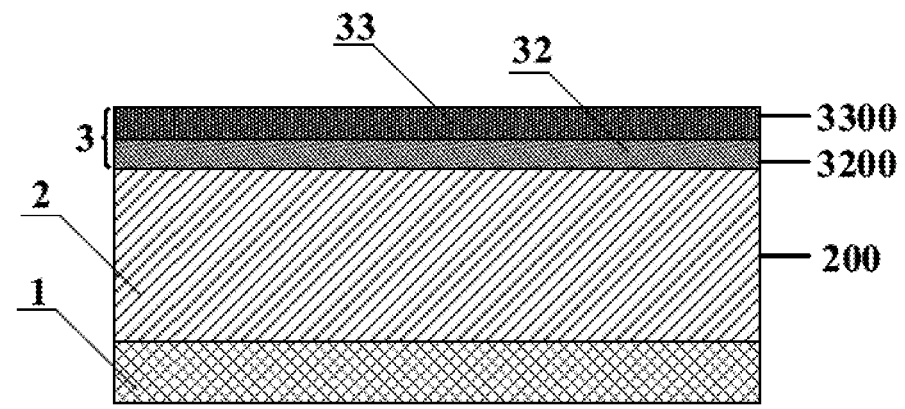

Referring to FIG. 14A, optionally, the method includes forming an insulating material sub-layer 3200 on a side of the first fluid channel material layer 200 away from the base substrate 1. Referring to FIG. 14B, the method includes forming a conductive material sub-layer 3300 on a side of the insulating material sub-layer 3200 away from the base substrate 1. Optionally, the insulating material sub-layer 3200 is formed using an insulating material. Optionally, the conductive material sub-layer 3300 is formed using a conductive material.

Figure 14C:
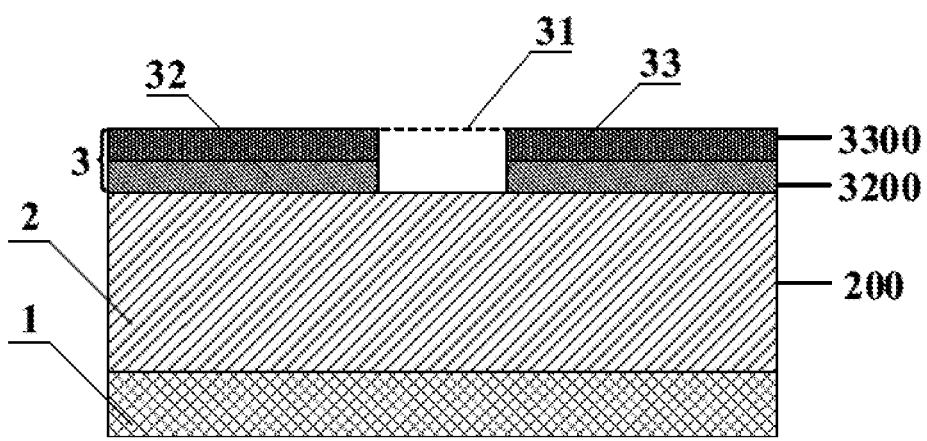

Referring to FIG. 14C, optionally, the method includes forming a conductive sub-layer 33 by patterning the conductive material sub-layer 3300; and form an insulating material sub-layer 32 by patterning the insulating material sub-layer 3200. The foundation layer 3 is formed by forming the conductive sub-layer 33 and the insulating sub-layer 32. Optionally, the foundation layer 3 is formed to have the foundation layer throughhole 31 extending through the foundation layer 3.

Figure 14D:
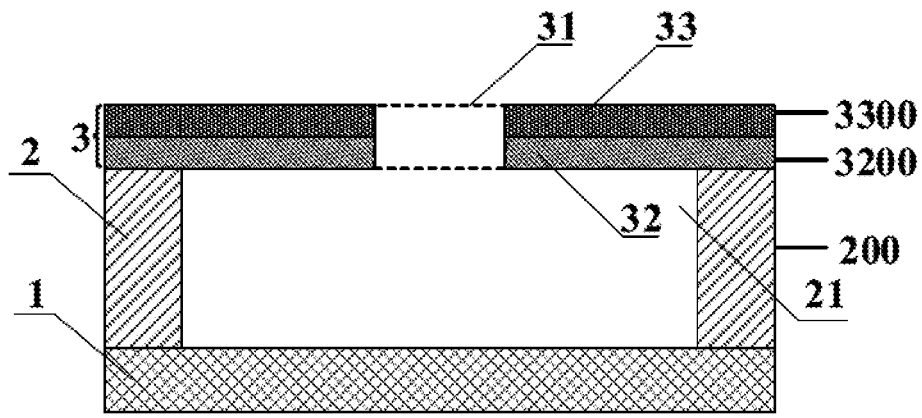
Figure 14D:
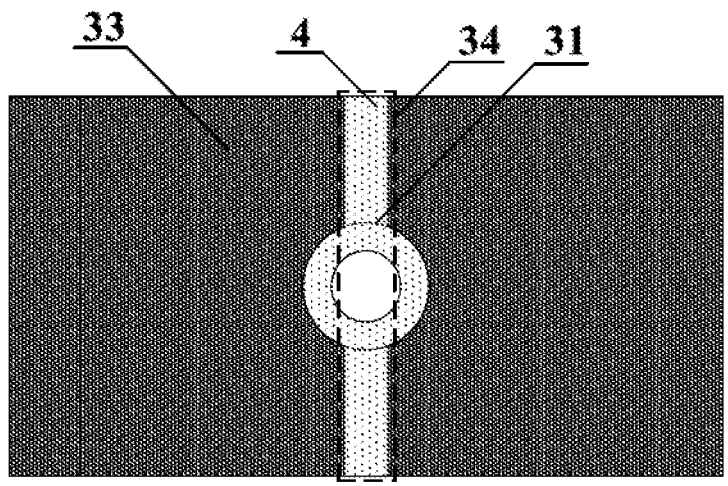

Referring to FIG. 14D, optionally, the method includes forming a first fluid channel layer 2 by patterning the first fluid channel material layer 200. Optionally, the first fluid channel layer 2 is formed to have the first fluid channel 21 passing through the first fluid channel layer 2. Optionally, the foundation layer throughhole 31 is formed to connect to the first fluid channel 21.

Optionally, the foundation layer 3 is formed as two parts spaced apart from each other by the foundation layer throughhole 31 and a split gap 34 shown in FIG. 14D' connected to the foundation layer throughhole 31. Optionally, the micropore layer 4 is formed to extend into the split gap 34 and fill in the split gap 34.

Figure 14E:
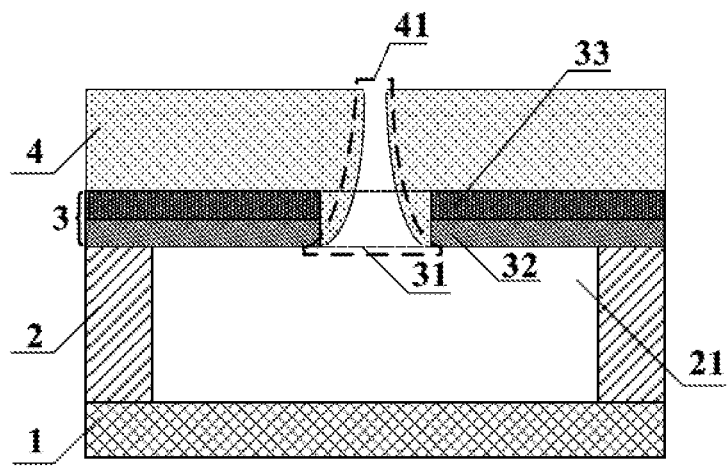

Referring to FIG. 14E, optionally, a wide of the split gap 34 in FIG. 14D' is relatively small. When the micropore layer 4 is deposited on the foundation layer 3, the micropore layer 4 can naturally fill in the split gap 34.

In some embodiment, in order to prevent an outmost conductive layer of the biosensor apparatus shown in the FIG. 4B, FIG. 5B, FIG. 6B, and FIG. 8B from exposing to air, the method further includes forming a capping layer covering an outmost conductive layer of the biosensor apparatus.

In some embodiments, referring to FIG. 3A, subsequent to forming the micropore layer 4, the method further includes forming a second fluid channel layer 12 on a side of the micropore layer 4 away from the base substrate 1 and having a second fluid channel 121 passing therethrough. Optionally, the second fluid channel 121 is formed to connect to the micropore 41.

In some embodiments, subsequent to forming the micropore layer 4, the method further includes forming a second fluid channel layer 12 on a counter substrate 1'. Optionally, the second fluid channel layer 12 includes a second fluid channel 121. Optionally, the method further includes attaching a side of the second fluid channel layer 12 away from the counter substrate 1' with a side of the micropore layer 4 away from the base substrate 1, to connect the first fluid channel 21, the micropore 41, and the second fluid channel 121 together.

Optionally, the second fluid channel layer 12 is formed using dry etching or wet etching.

In another aspect, the present disclosure also provides a biosensor chip including the biosensor apparatus described herein. Optionally, the biosensor chip includes multiple biosensor apparatus described herein. Optionally, the multiple biosensor apparatus can be arranged in array to detect multiple target molecules at the same time. Optionally, the biosensor chip has multiple functions including filtering out non-target molecules, detection target molecules, controlling movements of target molecules, and accumulating target molecules.

Figure 15:
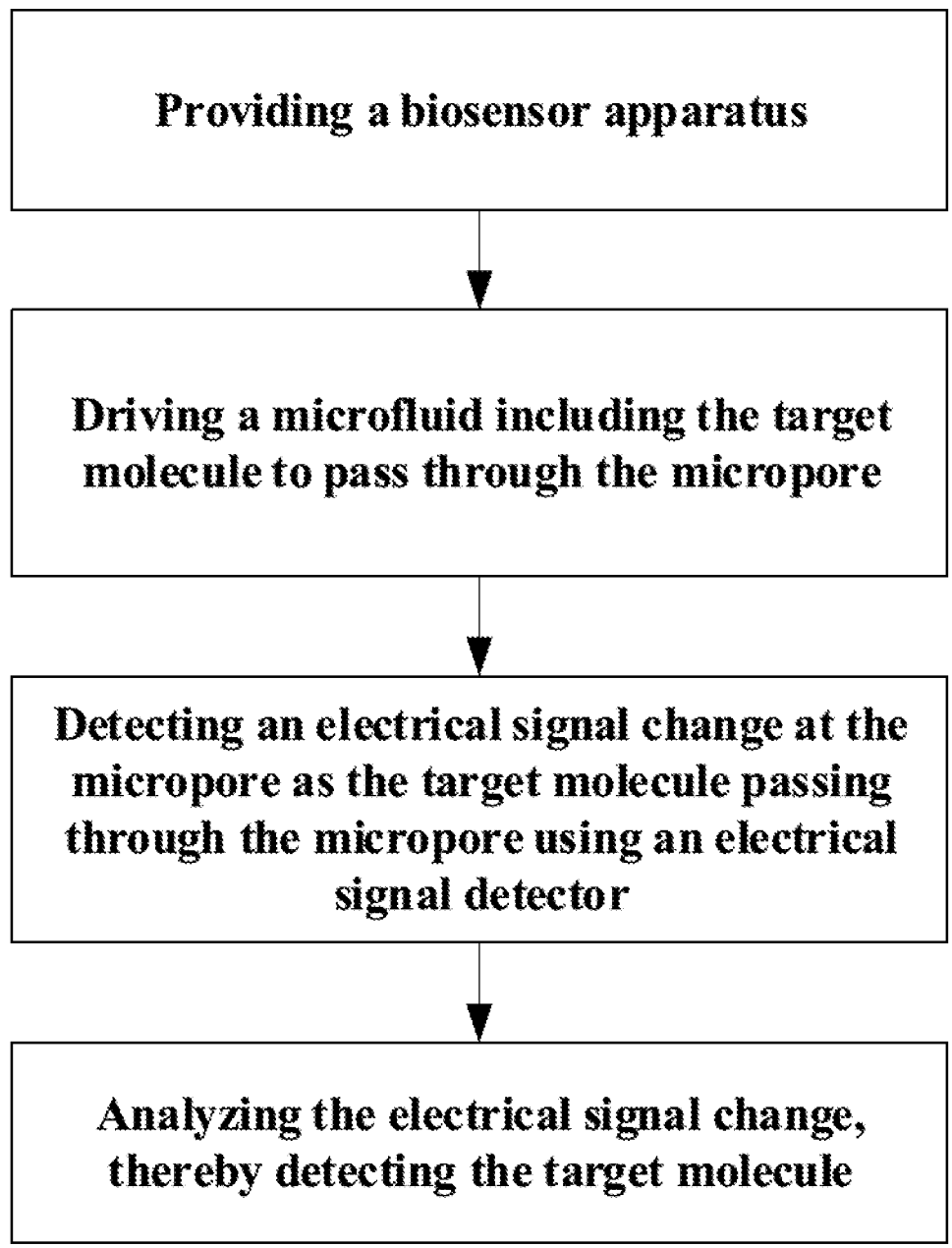
FIG. 15 is a schematic diagram illustrating a method of detecting a target molecule in some embodiments according to present disclosure.

In another aspect, the present disclosure also provides a method of detecting a target molecule. FIG. 15 is a schematic diagram illustrating a method of detecting a target molecule in some embodiments according to present disclosure. Referring to FIG. 15, in some embodiments, a method of detecting a target molecule includes providing the biosensor apparatus described herein; driving a microfluid having the target molecule to pass through the micropore; detecting an electrical signal change at the micropore as the target molecule passing through the micropore using an electrical signal detector; and analyzing the electrical signal change to detect the target molecule.

Optionally, in the process of providing the biosensor apparatus described herein, referring to FIG. 2A to FIG. 9C, the biosensor apparatus includes a micropore 41. Optionally, the micropore 41 is a nanopore having $10^{-9}$ meters in diameter.

Optionally, in the process of driving the microfluid having the target molecule to pass through the micropore, referring to FIG. 1, the biosensor apparatus is disposed in the detection system described herein to detect the target molecule 11. The driving controller 13 in the detection system drives the microfluid having the target molecule 11 to the first fluid channel 21, and drives the microfluid having the target molecule 11 to pass through the micropore 41. Optionally, the target molecules can be biomolecules. Examples of biomolecules include, but are not limited to, DNA molecule, a protein molecule, a cell or an amino acid.

Various appropriate ways may be used by the driving controller 13 to drive the microfluid. Examples of ways to drive the microfluid using the driving controller 13 include, but are not limited to, using electrophoresis, and using pressure pump.

Optionally, in the process of detecting an electrical signal change at the micropore as the target molecule passing through the micropore using an electrical signal detector, the detect system includes an electrical signal detection device. For example, when the biosensor apparatus 100 is disposed in the detection system, the biosensor apparatus is connected to the detection circuit 14, and the electrical signal detection device in the detection circuit 14 is also electrically connected to the biosensor apparatus 100.

Various appropriate electrical signal detection devices can be used based on different structures of the biosensor apparatus. Examples of electrical signal detection devices include, but are not limited to ammeters, voltmeters, and capacitance measuring devices.

In one example, the electrical signal detection device is an ammeter. The electrical signal change detected by the ammeter is a change of current vertically going through the micropore 41 of the biosensor apparatus 100. Or the electrical signal change detected by the ammeter is a change of current horizontally going through the micropore 41 of the biosensor apparatus 100.

In another example, the electrical signal detection device is a voltmeter. The electrical signal change detected by the voltmeter is a change of electric potential of the micropore 41 of the biosensor apparatus 100.

In another example, the electrical signal detection device is a capacitance measuring device. The electrical signal change detected by the capacitance measuring device is a change of a capacitance of the micropore 41 of the biosensor apparatus 100.

Optionally, in the process of analyzing the electrical signal change to detect the target molecule, different target molecules passing through the micropore 41 cause different electrical signal changes, so, by analyzing different electrical signal changes in the detection circuit 14, the different target molecules passing through the micropore 41 can be detected. For example, by analyzing different electrical signal changes in the detection circuit 14, different order of bases on the DNA chain passing through the micropore 41 can be detected.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A biosensor apparatus, comprising:
a base substrate;
a first fluid channel layer on the base substrate and having a first fluid channel passing therethrough;
a foundation layer on a side of the first fluid channel layer away from the base substrate, a foundation layer throughhole extending through the foundation layer to connect to the first fluid channel;
a micropore layer on a side of the foundation layer away from the base substrate, a micropore extending through the micropore layer to connect to the first fluid channel through the foundation layer throughhole; and
a first conductive layer on a side of the micropore layer away from the base substrate;
wherein the micropore layer extends into the foundation layer throughhole and at least partially covers an inner wall of the foundation layer throughhole;
the foundation layer comprises a conductive material; and
the micropore layer comprises an insulating material.

2. The biosensor apparatus of claim 1, wherein the first conductive layer is a unitary electrode, a first conductive layer throughhole extending through the first conductive layer to connect to the micropore.

3. The biosensor apparatus of claim 1, wherein the first conductive layer comprises two block electrodes spaced apart from each other and on two opposite side of a periphery of the micropore.

4. The biosensor apparatus of claim 1, wherein the foundation layer comprises an insulating material;
the micropore layer comprises an insulating material;
wherein the biosensor apparatus further comprises:
a detection electrode in the first fluid channel; and
a second conductive layer on a side of the micropore layer away from the base substrate.

5. The biosensor apparatus of claim 1, wherein the foundation layer comprises an insulating material;
the micropore layer comprises an insulating material;
wherein the biosensor apparatus further comprises a semiconductor layer on a side of the micropore layer away from the base substrate, a semiconductor layer throughhole extending through the semiconductor layer to connect to the micropore.

6. The biosensor apparatus of claim 1, wherein the foundation layer comprises an insulating material;
the micropore layer comprises a semiconductor material;
wherein the biosensor apparatus further comprises a third conductive layer on a side of the micropore layer away from the base substrate;
wherein the third conductive layer comprises two block electrodes spaced apart from each other and on two opposite side of a periphery of the micropore.

7. The biosensor apparatus of claim 1, wherein the foundation layer comprising:
an insulating sub-layer on a side of the first fluid channel layer away from the base substrate, the insulating sub-layer comprising an insulating material; and
a conductive sub-layer on a side of the insulating sub-layer away from the base substrate, the conductive sub-layer comprising a conductive material;
wherein the foundation layer is divided into two parts spaced apart from each other by the foundation layer throughhole and a split gap connected to the foundation layer throughhole; and
the micropore layer extends into the split gap and fills in the split gap.

8. The biosensor apparatus of claim 1, further comprising a capping layer covering an outmost conductive layer of the biosensor apparatus.

9. The biosensor apparatus of claim 1, further comprising a second fluid channel layer on a side of the micropore layer away from the base substrate and having a second fluid channel passing therethrough, the second fluid channel connected to the micropore.

10. A biosensor chip, comprising the biosensor apparatus of claim 1.

11. A method of fabricating a biosensor apparatus, comprising:
forming a first fluid channel layer on a base substrate and having a first fluid channel passing therethrough;
forming a foundation layer on a side of the first fluid channel layer away from the base substrate, a foundation layer throughhole formed to extend through the foundation layer to connect to the first fluid channel; and
forming a micropore layer on a side of the foundation layer away from the base substrate, a micropore formed to extend through the micropore layer to connect to the first fluid channel through the foundation layer throughhole;
subsequent to forming the micropore layer, forming a first conductive layer on a side of the micropore layer away from the base substrate;
wherein the micropore layer is formed to extend into the foundation layer throughhole and at least partially covers an inner wall of the foundation layer throughhole;
the foundation layer is formed using a conductive material; and
the micropore layer is formed using an insulating material.

12. The method of claim 11, wherein forming the first fluid channel layer and forming the foundation layer comprise:
forming a first fluid channel material layer on a base substrate;
forming a foundation material layer on a side of the first fluid channel material layer away from the base substrate;
patterning the foundation material layer to form the foundation layer, the foundation layer formed to have the foundation layer throughhole extending therethrough; and
patterning the first fluid channel material layer to form the first fluid channel layer, the first fluid channel layer formed to have the first fluid channel passing therethrough, the foundation layer throughhole formed to connect to the first fluid channel;
wherein forming the micropore layer comprises depositing a micropore layer material on a side of the foundation layer away from the base substrate;
wherein the micropore layer material is deposited onto an inner wall of the foundation layer throughhole.

13. The method of claim 11, wherein the foundation layer is formed using an insulating material; and
the micropore layer is formed using an insulating material;
wherein the method further comprises, prior to forming the first fluid channel layer, forming a detection electrode on the base substrate; and
subsequent to forming the micropore layer, forming a second conductive layer on a side of the micropore layer away from the base substrate.

14. The method of claim 11, wherein the foundation layer is formed using an insulating material; and
the micropore layer is formed using an insulating material;
wherein the method further comprises, subsequent to forming the micropore layer, forming a semiconductor layer on a side of the micropore layer away from the base substrate, a semiconductor layer throughhole formed to extend through the semiconductor layer to connect to the micropore.

15. The method of claim 11, wherein the foundation layer is formed using an insulating material; and
the micropore layer is formed using a semiconductor material;
wherein the method further comprises, subsequent to forming the micropore layer, forming a third conductive layer on a side of the micropore layer away from the base substrate, the third conductive layer formed to comprise two block electrodes spaced apart from each other and on two opposite side of a periphery of the micropore.

16. The method of claim 11, wherein the micropore layer is formed using an insulating material;
wherein forming the foundation layer comprises forming an insulating sub-layer on a side of the first fluid channel layer away from the base substrate, the insulating sub-layer formed using an insulating material; and
forming a conductive sub-layer on a side of the insulating sub-layer away from the base substrate, the conductive sub-layer formed using a conductive material;
wherein the foundation layer is formed as two parts spaced apart from each other by the foundation layer throughhole and a split gap connected to the foundation layer throughhole; and
the micropore layer is formed to extend into the split gap and fill in the split gap.

17. The method of claim 11, further comprising forming a capping layer covering an outmost conductive layer of the biosensor apparatus.

18. A method of detecting a target molecule, comprising:
providing the biosensor apparatus of claim 1;
driving a microfluid comprising the target molecule to pass through the micropore;
detecting an electrical signal change at the micropore as the target molecule passing through the micropore using an electrical signal detector; and
analyzing the electrical signal change, thereby detecting the target molecule.

* * * * *